US012635870B2

(12) United States Patent
Weinmann

(10) Patent No.: US 12,635,870 B2
(45) Date of Patent: May 26, 2026

(54) LARYNGOSCOPE

(71) Applicant: Maxwell Weinmann, Atlanta, GA (US)

(72) Inventor: Maxwell Weinmann, Atlanta, GA (US)

(73) Assignees: Maxwell Weinmann, Atlanta, GA (US);
Maria I. Marmarinos, Wellesley, MA (US)

( * ) Notice: Subject to any disclaimer, the term of this patent is extended or adjusted under 35 U.S.C. 154(b) by 0 days.

(21) Appl. No.: 18/674,780

(22) Filed: May 24, 2024

(65) Prior Publication Data

US 2025/0098952 A1     Mar. 27, 2025

Related U.S. Application Data

(63) Continuation of application No. 16/637,248, filed as application No. PCT/US2018/045391 on Aug. 6, 2018, now Pat. No. 11,992,193.

(Continued)

(51) Int. Cl.
A61B 1/267          (2006.01)
A61B 1/00           (2006.01)
(Continued)

(52) U.S. Cl.
CPC .......... A61B 1/267 (2013.01); A61B 1/00071 (2013.01); A61B 1/00105 (2013.01);
(Continued)

(58) Field of Classification Search
CPC ..................................................... A61B 1/267
See application file for complete search history.

(56) References Cited

U.S. PATENT DOCUMENTS 4,126,127  A     11/1978  May
4,570,614  A      2/1986  Bauman
(Continued)

FOREIGN PATENT DOCUMENTS

CN          201899479  U      7/2011
CN          105125163  A     12/2015
(Continued)

OTHER PUBLICATIONS

International Search Report and Written Opinion of the International Searching Authority directed to related International Patent Application No. PCT/US2018/045391, mailed Dec. 11, 2018; 9 pages.
(Continued)

*Primary Examiner* — Tessa M Matthews
(74) *Attorney, Agent, or Firm* — Sterne, Kessler, Goldstein & Fox P.L.L.C.

(57)               ABSTRACT
A laryngoscope includes a curved blade including a proximal end, a distal end, and a first channel. The laryngoscope also includes a handle and a second channel. The handle includes a non-electric light source, e.g., a chemiluminescent light source. A catalytic agent in the chemiluminescent light source is activated by pressure on the chemiluminescent light source to generate light that transmits along the first channel. The second channel is disposed proximate and through the blade and configured to provide at least one of oxygen, suction, and an instrumentation into the proximal end and out of the distal end of the blade.

14 Claims, 25 Drawing Sheets

Related U.S. Application Data

(60) Provisional application No. 62/542,125, filed on Aug. 7, 2017.

(51) Int. Cl.

| | |
|---|---|
| *A61B 1/015* | (2006.01) |
| *A61B 1/018* | (2006.01) |
| *A61B 1/06* | (2006.01) |
| *A61B 1/07* | (2006.01) |
| *A61B 90/30* | (2016.01) |
| *A61B 10/06* | (2006.01) |
| *A61B 17/32* | (2006.01) |
| *A61B 18/00* | (2006.01) |
| *A61B 18/20* | (2006.01) |
| *A61B 90/00* | (2016.01) |
| *A61M 25/09* | (2006.01) |
| *A61M 31/00* | (2006.01) |
| *A61N 5/10* | (2006.01) |

(52) U.S. Cl.
CPC .......... *A61B 1/00128* (2013.01); *A61B 1/015* (2013.01); *A61B 1/018* (2013.01); *A61B 1/06* (2013.01); *A61B 1/0669* (2013.01); *A61B 1/07* (2013.01); *A61B 90/30* (2016.02); *A61B 10/06* (2013.01); *A61B 17/320016* (2013.01); *A61B 2018/00595* (2013.01); *A61B 18/20* (2013.01); *A61B 2090/304* (2016.02); *A61B 2090/3987* (2016.02); *A61M 25/09* (2013.01); *A61M 31/00* (2013.01); *A61N 5/1007* (2013.01)

(56) References Cited

U.S. PATENT DOCUMENTS

| | | |
|---|---|---|
| 4,803,924 A | 2/1989 | Von Sloun |
| 5,179,938 A | 1/1993 | Lonky |
| 5,277,173 A | 1/1994 | Cantele |
| 5,287,848 A | 2/1994 | Cubb et al. |
| 5,551,946 A | 9/1996 | Bullard |
| 5,645,519 A | 7/1997 | Lee et al. |
| 5,676,635 A | 10/1997 | Levin |
| 5,819,727 A | 10/1998 | Linder |
| 5,888,195 A | 3/1999 | Schneider |
| 6,090,040 A | 7/2000 | Metro |
| 6,095,972 A | 8/2000 | Sakamoto |
| 6,106,458 A | 8/2000 | Ha |
| 6,189,533 B1 | 2/2001 | Simon et al. |
| 6,248,061 B1 | 6/2001 | Cook, Jr. |
| 6,843,769 B1 | 1/2005 | Gandarias |
| 7,445,753 B1 | 11/2008 | Kreis et al. |
| 7,608,040 B1 | 10/2009 | Dunst |
| 7,946,981 B1 | 5/2011 | Cubb |
| 8,864,657 B2 | 10/2014 | Tydlaska |
| 9,693,677 B2 | 7/2017 | McGrath |
| 9,867,531 B2 | 1/2018 | Pacey et al. |
| 10,285,571 B2 | 5/2019 | Rozenfeld et al. |
| 11,992,193 B2 | 5/2024 | Weinmann |
| 2001/0039949 A1 | 11/2001 | Loubser |
| 2002/0162557 A1 | 11/2002 | Simon |
| 2003/0137827 A1 | 7/2003 | Bouton et al. |
| 2003/0168059 A1 | 9/2003 | Pacey |
| 2004/0190975 A1 | 9/2004 | Goodman et al. |
| 2004/0210114 A1 | 10/2004 | Simon |
| 2005/0054903 A1 | 3/2005 | Cantrell |
| 2006/0207604 A1 | 9/2006 | Nelson et al. |
| 2006/0241494 A1 | 10/2006 | Bride |
| 2007/0161863 A1 | 7/2007 | Bentt |
| 2008/0058863 A1 | 3/2008 | Quintero et al. |
| 2009/0118624 A1 | 5/2009 | Bride |
| 2010/0004514 A1 | 1/2010 | Shalman et al. |
| 2010/0081875 A1 | 4/2010 | Fowler et al. |
| 2010/0121152 A1* | 5/2010 | Boedeker ............... A61B 1/267 |
| | | 600/187 |
| 2010/0249513 A1 | 9/2010 | Tydlaska |
| 2011/0120459 A1 | 5/2011 | Ramos |
| 2012/0033401 A1* | 2/2012 | Friedson ................... F21K 2/06 |
| | | 362/34 |
| 2012/0035502 A1 | 2/2012 | Menegazzi |
| 2012/0215069 A1 | 8/2012 | Bullard |
| 2014/0179998 A1 | 6/2014 | Pacey et al. |
| 2015/0099935 A1 | 4/2015 | Runnels |
| 2015/0164310 A1 | 6/2015 | Holt |
| 2021/0137376 A1* | 5/2021 | Vargo ................... A61B 1/0669 |

FOREIGN PATENT DOCUMENTS

| | | |
|---|---|---|
| CN | 106214115 A | 12/2016 |
| GB | 2517764 A | 3/2015 |
| JP | S61-170432 A | 8/1986 |
| JP | 2006-326111 A | 12/2006 |
| JP | 2008-514272 A | 5/2008 |
| JP | 2014-239881 A | 12/2014 |
| JP | 2016-502419 A | 1/2016 |
| RU | 2043068 C1 | 9/1995 |
| WO | WO 2003/075979 A2 | 9/2003 |
| WO | WO 2003/075979 A3 | 12/2003 |

OTHER PUBLICATIONS

International Preliminary Report on Patentability directed to related International Patent Application No. PCT/US2018/045391, issued Feb. 11, 2020; 8 pages.

Kamenou, I., "Miller laryngoscope," Life in the Fastlane Medical Eponym Library, Nov. 3, 2020 (accessed on Sep. 28, 2021 at https://litfl.com/miller-laryngoscope/); 9 pages.

Description and Catalog Record for "Miller Laryngoscope," Wood Library Museum of Anesthesiology, Feb. 11, 2014 (accessed on Sep. 28, 2021 at https://www.woodlibrarymuseum.org/museum/miller-laryngoscope/); 5 pages.

\* cited by examiner

100

LARYNGOSCOPE

CROSS-REFERENCE TO RELATED APPLICATIONS

This application is a continuation of U.S. patent application Ser. No. 16/637,248, filed Feb. 6, 2020, which is a National Stage Entry of PCT International Application No. PCT/US2018/045391, filed Aug. 6, 2018, which claims the benefit of U.S. Provisional Patent Application No. 62/542,125, filed Aug. 7, 2017, the entireties of which are all incorporated herein by reference.

BACKGROUND

Field

This disclosure generally relates to laryngoscopes.

Related Art

Advanced airway management is one of the most critical medical procedures practiced in the operating room, emergency department, intensive care unit, in urgent care centers, in the field, and on the battlefield in both adult and pediatric patients. The ability to create an open pathway to a patient's lung(s) in a safe, reliable, and efficient manner is a critical skill that can be enhanced by the creation of quality airway intubation and visualization devices.

Laryngoscopes were introduced in the 1940s and are widely used today for airway management. There are approximately 21 million laryngoscopy procedures performed every year in the United States. However, currently available laryngoscopes have many limitations and are prone to failure by multiple unpredictable means. As these devices are typically used in emergency situations, failure is not acceptable.

One of the shortcomings of the existing laryngoscopes is contamination in varying degrees. Incomplete disinfection and cross contamination are serious nosocomial problems that have been demonstrated to occur with reusable laryngoscope handles and blades. Although some laryngoscopes are claimed to be "disposable," they are not truly disposable in their entirety. That is, only the blade portion of the device is disposable, while the handle portion is reusable and must be maintained carefully.

There is the further risk associated with the handling of an electrical device as most of the traditional laryngoscopes use electric light sources to provide adequate visualization of the airway during the procedures. Electric light sources, such as batteries, are heavy and may cause reliability and safety issues when used in human bodies.

Another common issue of the conventional laryngoscopes is the large size and heavy weight due to the design and material (e.g., metals) used for the device. The bulky size of some conventional laryngoscopes is cumbersome, obscures adequate visualization of the airway entrance, and prevents manipulation of the trajectory of an endotracheal tube.

Another problem associated with currently available laryngoscopes is dental trauma and detachment. This occurs because of difficulty in placement and visualization, the metal blades, and the weight associated with the entire device bearing down on dentition.

A further risk of current laryngoscopes exists for soldiers in the battlefield. When a detectable light source is used in combat triage, white light can betray the location of troops and endanger them.

SUMMARY

This disclosure generally relates to laryngoscopes. According to an aspect of the present disclosure, a laryngoscope includes a curved blade having a proximal end, a distal end, and a first channel. The laryngoscope also includes a handle and a second channel. The handle includes a non-electric light source including a chemiluminescent light source. A catalytic agent in the chemiluminescent light source is activated by pressure on the chemiluminescent light source to generate light that transmits along the first channel. The second channel is disposed proximate and through the blade and configured to provide at least oxygen, suction, or an instrumentation into the proximal end and out of the distal end of the blade.

According to another aspect of the present disclosure, a handle of a laryngoscope includes a non-electric light source and a connector. The non-electric light source may include a chemiluminescent light source. A catalytic agent in the chemiluminescent light source is activated by pressure on the catalytic agent within the chemiluminescent light source to generate light. The connector is configured to removably attach a blade to the handle. The connector includes an optical interface configured to couple the light generated by the chemiluminescent light source to a light channel in the blade.

According to still another aspect of the present disclosure, a blade of a laryngoscope includes a curved body and a first channel. The curved body widens out from a proximal end to a distal end. The first channel is configured to transmit light. At least a part of the body is configured to reflect the light.

This Summary is provided merely for purposes of illustrating some embodiments to provide an understanding of the subject matter described herein. Accordingly, the above-described features are merely examples and should not be construed to narrow the scope or spirit of the subject matter in this disclosure. Other features, aspects, and advantages of this disclosure will become apparent from the following Detailed Description, Figures, and Claims.

BRIEF DESCRIPTION OF THE FIGURES

The accompanying drawings, which are incorporated herein and form part of the specification, illustrate the presented disclosure and, together with the description, further serve to explain the principles of the disclosure and enable a person of skill in the relevant art(s) to make and use the disclosure.

Figure 1:
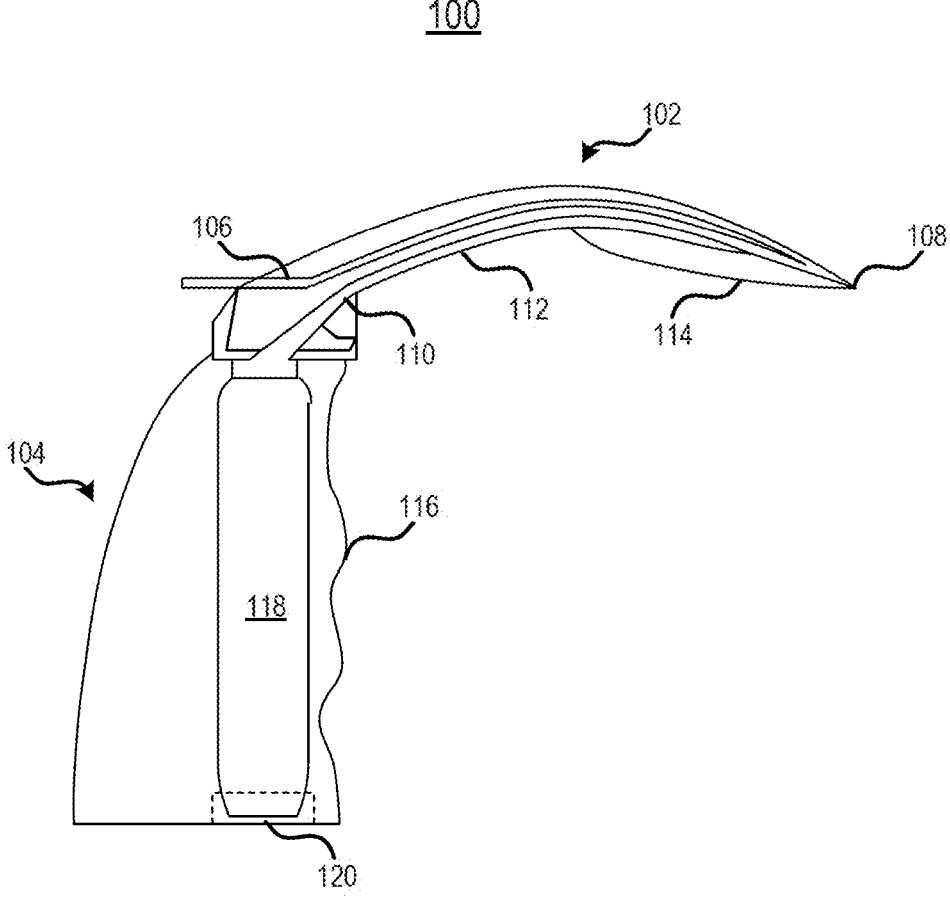
FIG. 1 is a schematic side cross-sectional view of a laryngoscope in accordance with an embodiment.

The presented disclosure is described with reference to the accompanying drawings. In the drawings, generally, like reference numbers indicate identical or functionally similar elements. Additionally, generally, the left-most digit(s) of a reference number identifies the drawing in which the reference number first appears.

DETAILED DESCRIPTION

As described above, there is an unmet medical need for high quality, reliable, and cost-effective laryngoscopes that overcome the shortcomings of products that are available in the marketplace today. The benefits of a disposable, light-weight laryngoscope with a reliable self-contained non-electric light source, as disclosed in the present disclosure, provide clear advantages to traditional laryngoscopes and their methods of illumination.

According to some embodiments, the laryngoscopes may include non-electric light sources such as a chemiluminescent light source that can generate light through a chemical reaction that takes place inside a chemiluminescent cartridge. The cartridge may be activated while within the handle or may be activated prior to insertion into the handle. The non-electric light source may provide light at different wavelengths, for example, chosen based on the situation. The wavelengths can range from visible to infrared light. Compared with traditional laryngoscopes using electric light sources, the laryngoscopes in the present disclosure are more reliable and safe during the procedures.

According to some embodiments, an optical fiber or a waveguide may run through the blade, which conducts the light generated by the cartridge through the blade to illuminate the oral cavity and airway entrance of a patient. The blade may be transparent with the exception of the bottom (e.g., ventral) of the blade, which may be, at least in part, reflective to enhance luminosity. Thus, the field of vision for the operator at the airway entrance can be optimized by the laryngoscopes in the present disclosure.

According to some embodiments, the laryngoscopes may be made of non-metal materials, such as plastics, with an integrated design for a curved blade or a straight blade and an ergonomic handle within which the non-electric light source resides, e.g., a chemiluminescent cartridge. The blade may be thin and curved along its length to match the anatomy of the mouth and larynx, or it may be straight. The blade may also have a small lateral ridge to facilitate capture of the tongue. Through using plastics, both the weight and size of the device can be reduced, thereby reducing the risk of fractures, bleeding, and injury to the teeth and mouth, as well as making handling and carrying of the device easier.

According to some embodiments, the laryngoscope may have the ability to provide oxygen at various flow rates and concentrations, suction, or facilitate insertion of different instrumentations into the pharynx and airway via a channel which runs the length of the blade and may be attached to an oxygen or suction source through a connector in the rear of the device. For example, this can be done to allow the laryngoscope to be used even when there is swollen or traumatized vocal cords. Therefore, should there be any difficulty in identifying the vocal cords, the operator may continue to provide a stream of life-saving oxygen. Alternatively, if the airway is contaminated with blood, mucus, vomit, etc., suction may be applied as well. This can be achieved without removing the laryngoscope and keeps the operator's hand or hands free, unlike in the traditional situation.

According to some embodiments, the laryngoscopes may have an opening in the enclosure of the handle so that the chemiluminescent light source may be inserted in or removed from the enclosure via the opening.

According to some embodiments, the chemiluminescent light source may be activated by various means, such as torsional pressure via a rotational cam, or compression, prior to or after being inserted into the handle. The replacement and activation of the chemiluminescent light source are thus easy to operate by the operator in either an elective or emergent situation.

According to some embodiments, the laryngoscopes may be impervious to sand and moisture to be used in different environments, e.g., including battlefields.

According to some embodiments, the entire laryngoscope may be disposable or used repeatedly on a single patient in the same situation to avoid cross contamination.

FIG. 1 is a schematic side cross-sectional view of a laryngoscope 100 in accordance with an embodiment. Laryngoscope 100 includes a blade 102, a handle 104, and an auxiliary channel 106.

In an embodiment, blade 102 may be curved in the length direction between a distal end 108 (e.g., the tip of blade 102) and a proximal end 110 (e.g., the end towards the operator during laryngoscope procedures). The curvature of blade 102 may be set to match the anatomy of the mouth and larynx of patients, such as between 20 and 60 degrees. In some embodiments, the thickness of blade 102 may be uniform, such as between 3 and 24 millimeters (mm). In some embodiments, the thickness of blade 102 may change in the length direction, for example, gradually increasing from distal end 108 to proximal end 110. In some embodiments, the thickness of blade 102 may change in the width direction, for example, gradually decreasing from the middle to the edges, or vice versa.

It is understood by a person of ordinary skill in the art that in the present disclosure, a blade, e.g., blade 102, has two major surfaces, including the top (e.g., dorsal) of the blade that is toward the patient's tongue and lower jaw during the laryngoscope procedures, and the bottom (e.g., ventral) of the blade that is toward the patient's upper jaw during the laryngoscope procedures.

In an embodiment, the body of blade 102 is made from a non-metal material including, for example, plastic materials such as polycarbonate (PC), poly(methyl methacrylate) (PMMA), polyether ether ketone (PEEK), polyphenylsulfone (PPSU), etc., carbon fiber, and composite materials such as fiber-reinforced polymers (FRPs) or ceramic composites. The non-metal materials may optimize weight reduction of blade 102 and overcome the problem of heavy and cumbersome traditional blades. The non-metal materials may also reduce risk of injury to the patient during use, e.g., to the patient's teeth. It is to be appreciated that in some embodiments, certain metal materials, metal alloy materials, or metal composite materials with a light weight, such as aluminum, titanium, or alloys thereof, may be used as the body material of blade 102.

In an embodiment, blade 102 also includes a light channel 112 and a lateral ridge 114. Light channel 112 may be one of the two conduit structures on or in blade 102 (i.e., a first channel) that is operative to transmit light through it (i.e., an optical path). Lateral ridge 114 is disposed on the top of blade 102 and in the vicinity of or at distal end 108. In some embodiments, lateral ridge 114 is disposed on the outer edge of the top of blade 102. Lateral ridge 114 is configured to facilitate capture and direction of the tongue during the procedures. For example, lateral ridge 114 may allow the operator to capture and manually move the patient's tongue out of the field of view in order to optimize the visualization of the patient's airway for the operator. This may be useful, for example, after an allergic reaction or trauma to the tongue. In some embodiments, the size of lateral ridge 114 is set so that damage to the teeth or tongue caused by motion of blade 102 can be reduced.

In an embodiment, light channel 112 is fixed to the top of blade 102 along the length direction. In some embodiments, light channel 112 may traverse the entire length of blade 102 between distal end 108 and proximal end 110. In some embodiments, light channel 112 may traverse part of the entire length of blade 102, for example, starting from proximal end 110, but not reaching distal end 108. In this embodiment, light channel 112 is configured to transmit light through blade 102 to illuminate the patient's oral cavity and airway entrance, e.g., the larynx, during the laryngoscope procedures. Light channel 112 may include any structure that can conduct light, such as optical fibers or waveguides. As described above, depending on the light generated from handle 104, light channel 112 can transmit light at the corresponding wavelength(s), such as in the range of infrared to visible light. The various wavelengths of light that can be transmitted by light channel 112 accommodate different clinical situations in which laryngoscope 100 is used, such as using infrared light that is "invisible" to night-vision detectors when laryngoscope 100 is used in the battlefields.

In an embodiment, handle 104 includes an enclosure 116 and a non-electric light source 118 residing in enclosure 116. Enclosure 116 may be any suitable structure in handle 104, e.g., walls that form a cavity in which non-electric light source 118 is positioned within and held by the enclosure. Non-electric light source 118 is configured to generate light at a wavelength that transmits along light channel 112. Non-electric light source 118 may be, e.g., a chemiluminescent light source by which light is generated from a chemical reaction as described below. It is to be appreciated that in some embodiments, other non-electric light sources, such as, but not limited to, bioluminescent light sources, crystalloluminescent light sources, thermoluminescent light sources, photoluminescent light sources, etc., may be used as non-electric light source 118. By replacing electric light sources that require batteries with non-electric light source 118, a lighter weight, higher reliability, and increased safety can be achieved for laryngoscope 100. The generated light of non-electric light source 118 may last for hours, providing sufficient time to intubate a patient in either an elective or emergent situation.

In an embodiment, handle 104 is an ergonomic handle for ease of use by the operator. Enclosure 116 of handle 104 can include an opening 120 at the bottom surface from which non-electric light source 118 can be inserted in or removed from handle 104, e.g., for replacement. Opening 120 may be a lockable hatch with, e.g., a pivoting, snap-on, screw-on cap, or trap door, etc. When opening 120 is unlocked, non-electric light source 118, such as a chemiluminescent cartridge, can be inserted in or removed from enclosure 116 of handle 104. It is to be appreciated that in other embodiments, opening 120 may be on different parts of enclosure 116, for example, a side surface.

In an embodiment, the body of handle 104 is made from a non-metal material including plastic materials, such as PC, PMMA, PEEK, PPSU, etc., carbon fiber, or composite materials such as FRPs or ceramic composites. The non-metal materials may optimize weight reduction of handle 104 and overcome the problem of heavy and cumbersome traditional handles. It is to be appreciated that in some embodiments, certain metal materials, metal alloy materials, or metal composite materials with light weights, such as aluminum, titanium, or alloys thereof, may be used as the body material of handle 104. The materials of making blade 102 and handle 104 may be the same or different.

In an embodiment, auxiliary channel 106 is disposed proximate and through blade 102. Auxiliary channel 106 may be one of the two conduit structures on or in blade 102 (i.e., a second channel) that is operative to provide additional functions as described below in detail. The inlet of auxiliary channel 106 may be in the vicinity of or at proximal end 110, and the outlet of auxiliary channel 106 may be in the vicinity of or at distal end 108. Auxiliary channel 106 traverses the length of blade 102 and is proximate to of light channel 112. In some embodiments, auxiliary channel 106 may be parallel to light channel 112 along the length direction of blade 102. In this embodiment, auxiliary channel 106 is configured to provide oxygen, suction, an instrumentation, etc. into proximal end 110 and out of distal end 108 of blade 102. Auxiliary channel 106 can behave as a suction device when connected through to an external suction device for suction of debris (e.g., blood, mucus, vomit, etc.), which may obscure visualization of the airway and thereby impeding successful intubation. Auxiliary channel 106 may also provide a means of delivering oxygen to the patient when connected to an external oxygen source. This can be achieved without removing laryngoscope 100 and keeps the operator's hand or hands free, unlike in the traditional situation. Additionally or alternatively, various types of instrumentations can be inserted through auxiliary channel 106 into the vocal cords or airway of the patient during the procedures. The instrumentation includes, for example, but is not limited to, a wire, a cautery device, a laser, a fiber optics, a biopsy forceps, placement of radiotherapeutic markers and materials, a wire guided scalpel, placement of topical medications and therapies, etc.

Figure 2:
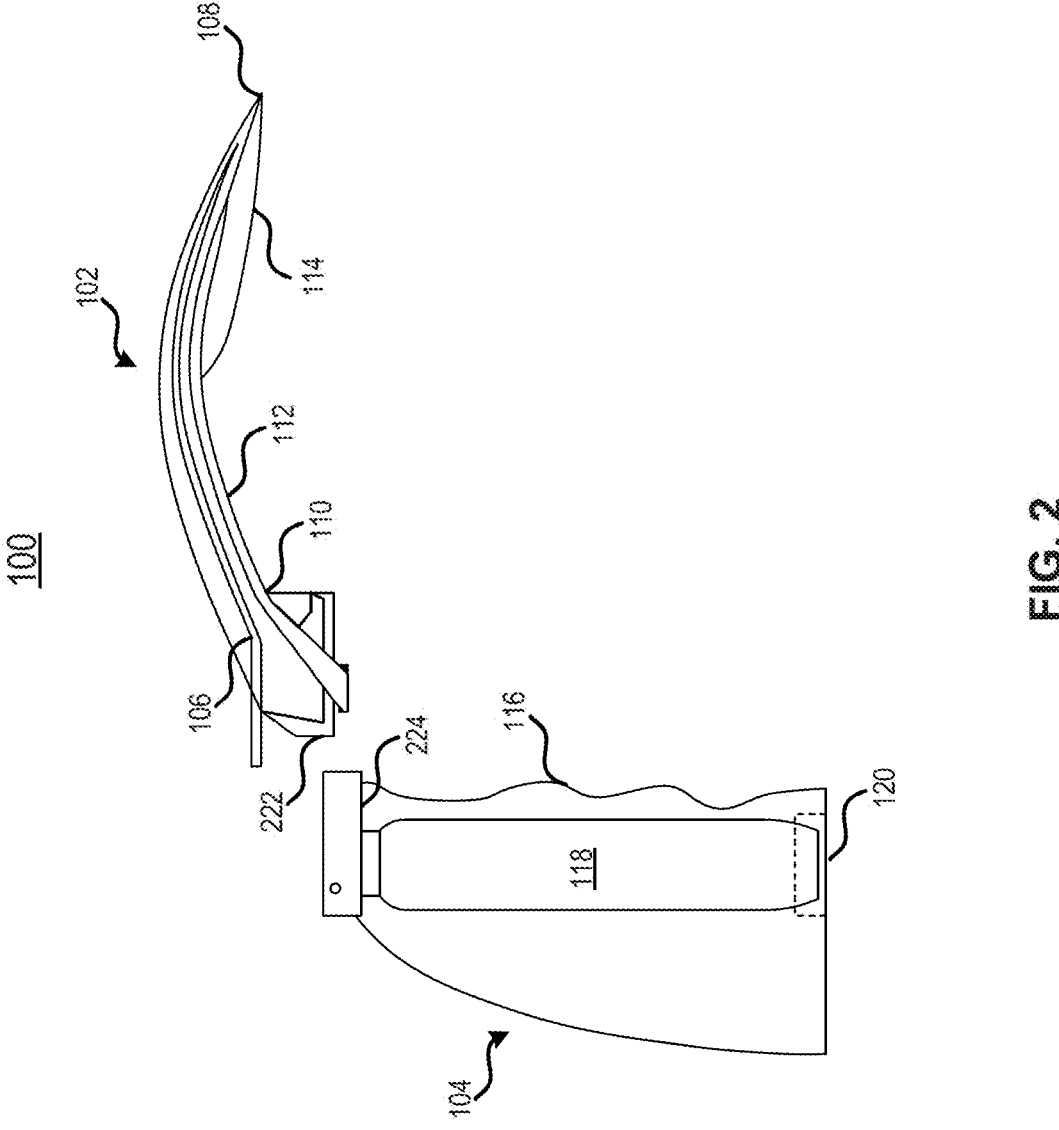
FIG. 2 is a schematic side cross-sectional view of the laryngoscope in FIG. 1 with a blade detached from a handle in accordance with an embodiment.

FIG. 2 is a schematic side cross-sectional view of laryngoscope 100 in FIG. 1 with blade 102 detached from handle 104, in accordance with an embodiment. In this embodiment, blade 102 is removably attached to handle 104 via a connector 222 of blade 102 and a connector 224 of handle 104. Connectors 222 and 224 may mate with one another so that blade 102 can attach to and detach from handle 104 through various mechanisms, such as pivoting, snap-on, screw-on, etc. In addition to providing the mechanical attachment between blade 102 and handle 104, connectors 222 and 224 also provide an optical interface configured to couple the light generated by non-electric light source 118 in handle 104 to light channel 112 in blade 102. As blade 102 can be easily detached from handle 104, blade 102 may be replaced after every single use or several uses on the same patient in the same situation to avoid cross contamination. It is to be appreciated that in some embodiments, blade 102 may be fixed to handle 104 by mechanical fasteners, adhesives, or any suitable fixation means. In some embodiments, blade 102 and handle 104 may be formed integrally from the same material.

Figure 3:
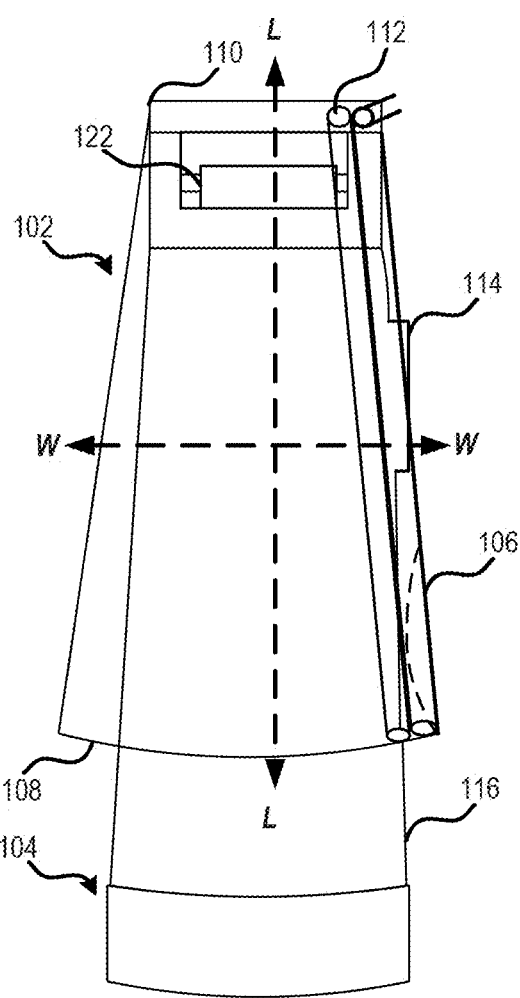
FIG. 3 is a schematic front view of the laryngoscope in FIG. 1 in accordance with an embodiment.

FIG. 3 is a schematic front view of laryngoscope 100 in FIG. 1 in accordance with an embodiment. Proximal end 110 to distal end 108 are two ends of blade 102 in the length direction (shown as L-L in FIG. 3). The width direction (shown as W-W in FIG. 3) is perpendicular to the length direction L-L. In this embodiment, the body of blade 102 widens out from proximal end 110 to distal end 108. That is, the width of blade 102 gradually increases from proximal end 110 to distal end 108. In some embodiments, the width of blade 102 at distal end 108 may be up to 20% larger than the width of blade 102 at proximal end 110. Such design of blade 102, along with lateral ridge 114, can facilitate capture of the tongue and optimizing the field of vision for the operator during the procedures.

As shown in FIG. 3, in this embodiment, auxiliary channel 106 and light channel 112 are proximate to one another at one edge of blade 102. In some embodiments, auxiliary channel 106 and light channel 112 may be disposed apart from one another, for example, at two edges of blade 102, respectively. Or one of auxiliary channel 106 and light channel 112 may be disposed in the middle of blade 102 in the width direction, and the other one of auxiliary channel 106 and light channel 112 may be disposed at one edge of blade 102. In some embodiments, auxiliary channel 106 and light channel 112 may be proximate to one another in the middle of blade 102 in the width direction (shown as W-W in FIG. 3). Also, as shown in FIG. 3, in this embodiment, each of auxiliary channel 106 and light channel 112 extends from proximal end 110 of blade 102 to distal end 108 of blade 102, i.e., traversing the entire length of blade 102. As described above, in some embodiments, one or both of auxiliary channel 106 and light channel 112 may traverse only a portion of the entire length of blade 102.

Figure 4:
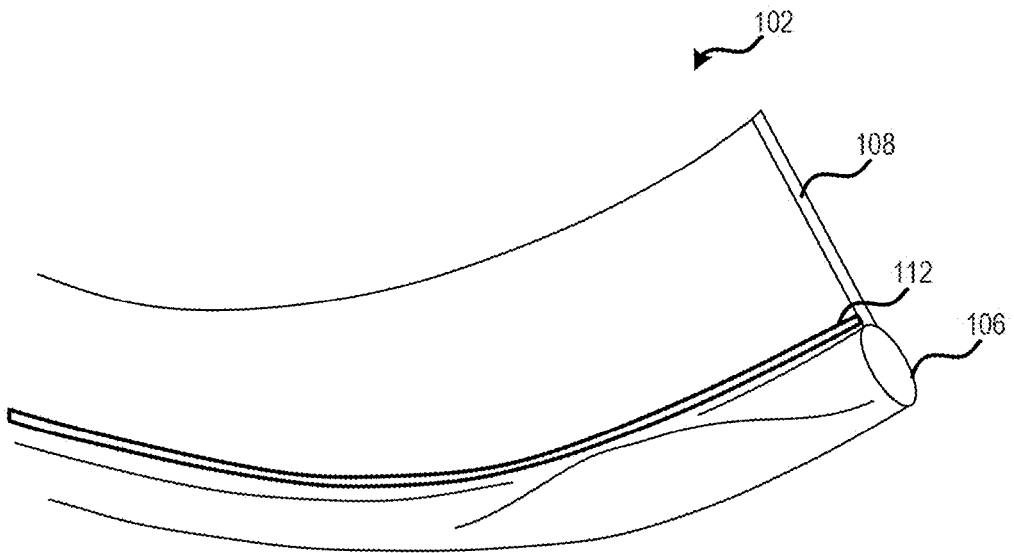
FIG. 4 is a schematic side view of a blade of the laryngoscope in FIG. 1 in accordance with an embodiment.

FIG. 4 is a schematic side view of blade 102 of laryngoscope 100 in FIG. 1 in accordance with an embodiment. In this embodiment, blade 102 may be made of a material that is transparent with respect to the wavelength of the light generated by non-electric light source 118 so that the light transmitted along light channel 112 can pass through blade 102 to illuminate the oral cavity and airway entrance of the patient.

Figure 5:
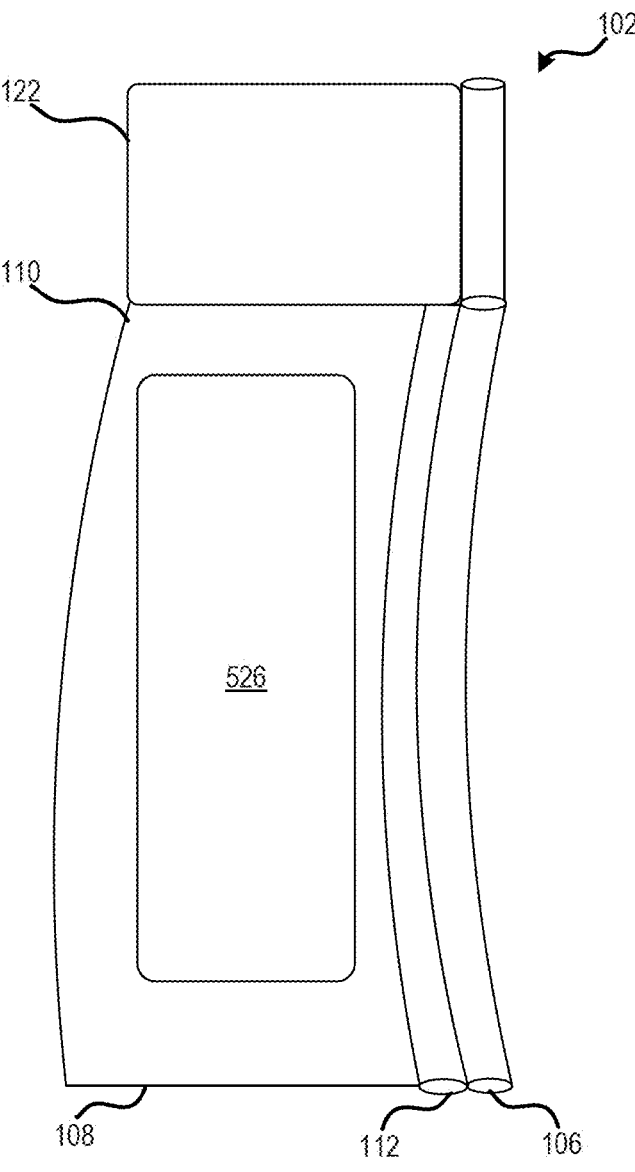
FIG. 5 is a schematic bottom view of a blade of the laryngoscope in FIG. 1 with a reflective surface in accordance with an embodiment.

FIG. 5 is a schematic bottom view of blade 102 of laryngoscope 100 in FIG. 1 with a reflective surface 526 in accordance with an embodiment. In this embodiment, blade 102 has reflective surface 526 on the bottom of the body. Reflective surface 526 is made of a material that is reflective with respect to the light at the wavelength generated by non-electric light source 118 and transmitted along light channel 112. As a result, during the procedures, luminosity of the light can be enhanced by reflective surface 526 of blade 102. Reflective surface 526 may be formed by applying light-reflection coatings (e.g., mirror coatings) on the bottom of the body of blade 102, such as aluminum, silver, gold coatings, etc. In this embodiment, the remaining parts of blade 102 are made from a plastic material, which is transparent to visible light. In some embodiments, reflective surface 526 may cover the entire bottom surface of blade 102.

Figure 6:
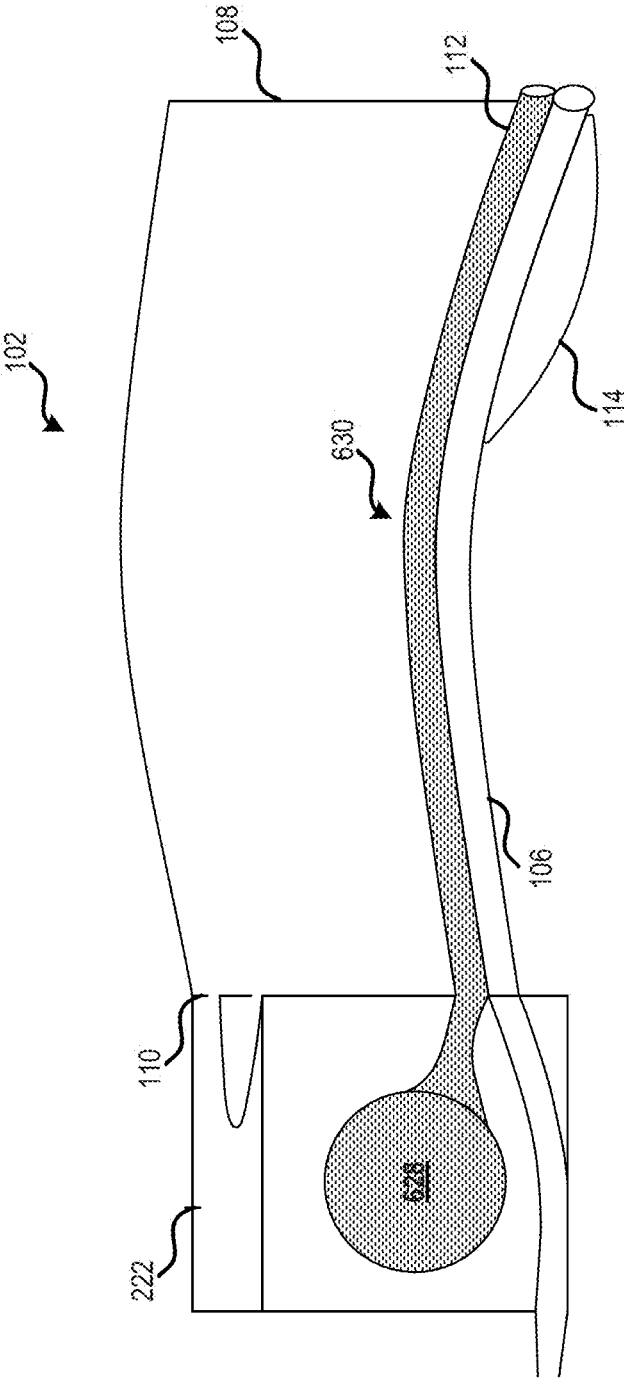
FIG. 6 is a schematic perspective view of a blade and a connector of the laryngoscope in FIG. 1 with an optical path in accordance with an embodiment.
Figure 7:
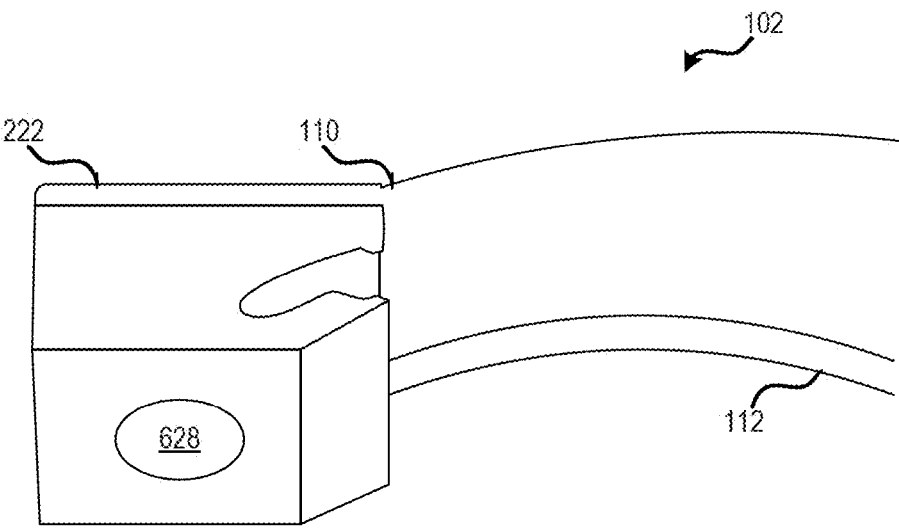
FIG. 7 is a schematic perspective view of a connector attached to a blade of the laryngoscope in FIG. 1 in accordance with an embodiment.

FIGS. 6 and 7 are schematic perspective views of blade 102 and connector 222 attached to blade 102 of laryngoscope 100 in FIG. 1 with an optical path in accordance with an embodiment. In this embodiment, connector 222 of blade 102 includes an optical interface 628 configured to couple the light from non-electric light source 118 in handle 104 to light channel 112 in blade 102. An optical path 630 (dotted region) is thus formed along the length direction of blade 102 in which the light is transmitted from optical interface 628 in connector 222 to the end of light channel 112 at distal end 108 of blade 102. Depending on the structure of light channel 112, e.g., an optical fiber or a waveguide, optical interface 628 with suitable optical properties, e.g., refractive index, may be formed in connector 222. In some embodiments, optical interface 628 may include an optical fiber connector when light channel 112 includes an optical fiber. In some embodiments, optical interface 628 may include a waveguide flange when light channel 112 includes a waveguide.

Figure 8:
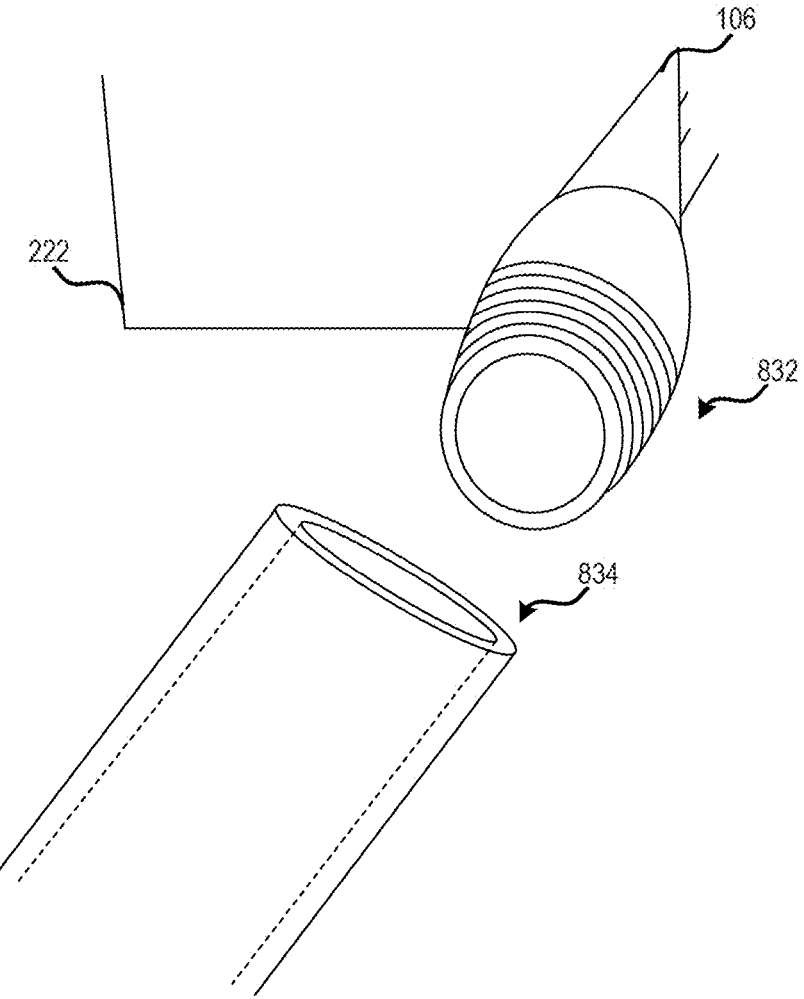
FIG. 8 is a schematic perspective view of an adaptor connecting an oxygen tube to a channel of the laryngoscope in FIG. 1 in accordance with an embodiment.

FIG. 8 is a schematic perspective view of an adaptor 832 of connector 222 connecting an oxygen tube 834 to auxiliary channel 106 of laryngoscope 100 in FIG. 1 in accordance with an embodiment. In this embodiment, connector 222 of blade 102 includes adaptor 832 configured to couple oxygen tube 834 to auxiliary channel 106. The other end of oxygen tube 834 may be connected to an oxygen source, such as a medical gas supply, so that oxygen can be provided to the patient via laryngoscope 100 during the laryngoscope procedures without removing laryngoscope 100. It is to be appreciated that in some embodiments, adaptor 832 may be configured to couple an external suction tube to auxiliary channel 106. The other end of the external suction tube may be connected to a suction machine so that debris and fluids can be removed during the laryngoscope procedures. In some embodiments, adaptor 832 may be configured to couple instrumentation so that the instrumentation can be inserted into the patient's mouth and/or larynx via auxiliary channel 106. As described above, the instrumentation may be a wire, a cautery device, a laser, a fiber optics, a biopsy forceps, placement of radiotherapeutic markers and materials, a wire guided scalpel, placement of topical medications and therapies, etc. Adaptor 832 may be the corresponding adaptor depending on the type of the instrumentation. It is also to be appreciated that in some embodiments, adaptor 832 may be in connector 224 of handle 104. It is also to be appreciated that in some embodiments, adaptor 832 may be configured to couple more than one oxygen or suction sources and/or instrumentations.

Figure 9:
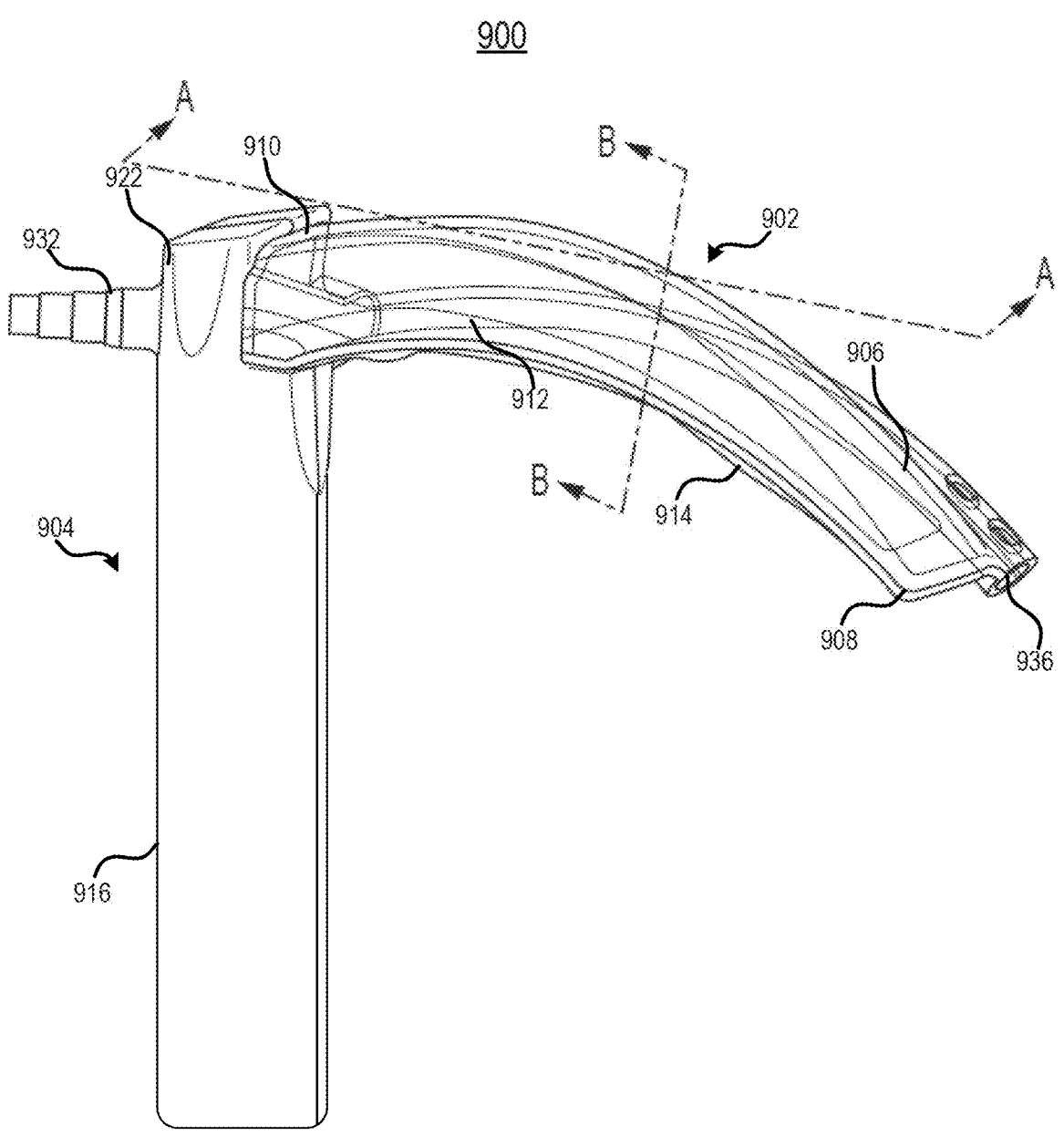
FIG. 9 is a perspective view of an example of the laryngoscope in FIGS. 1-8 in accordance with an embodiment.

FIG. 9 is a perspective view of an example of laryngoscope 900 in accordance with an embodiment. In this embodiment, a laryngoscope 900 includes a curved blade 902, an ergonomic handle 904, and an auxiliary channel 906. Blade 902 includes a distal end 908 and a proximal end 910 in the length direction. Blade 902 also includes a light channel 912 extending from proximal end 910 to distal end 908 of blade 902. Blade 902 further includes a lateral ridge 914 at the top (dorsal) of the body of blade 902.

In this embodiment, handle 904 includes an enclosure 916 in which a non-electric light source, e.g., a chemiluminescent light source (not shown) resides. Handle 904 also includes a connector 922 on top of enclosure 916. Connector 922 is configured to attach blade 902 to handle 904. Connector 922 includes an adaptor 932 connected to auxiliary channel 906 inside blade 902 and configured to couple an oxygen source, a suction source, and/or an instrumentation to auxiliary channel 906. Auxiliary channel 906 extends from adaptor 932 to proximal end 910 and ends at an outlet 936 at distal end 908 of blade 902. For example, oxygen, suction, instrumentations, etc. may be provided to the patient via outlet 936 during the procedures. It is understood that functions and structures of similar components in laryngoscope 100 can be used in laryngoscope 900, so they are not repeated in describing laryngoscope 900.

Figure 10:
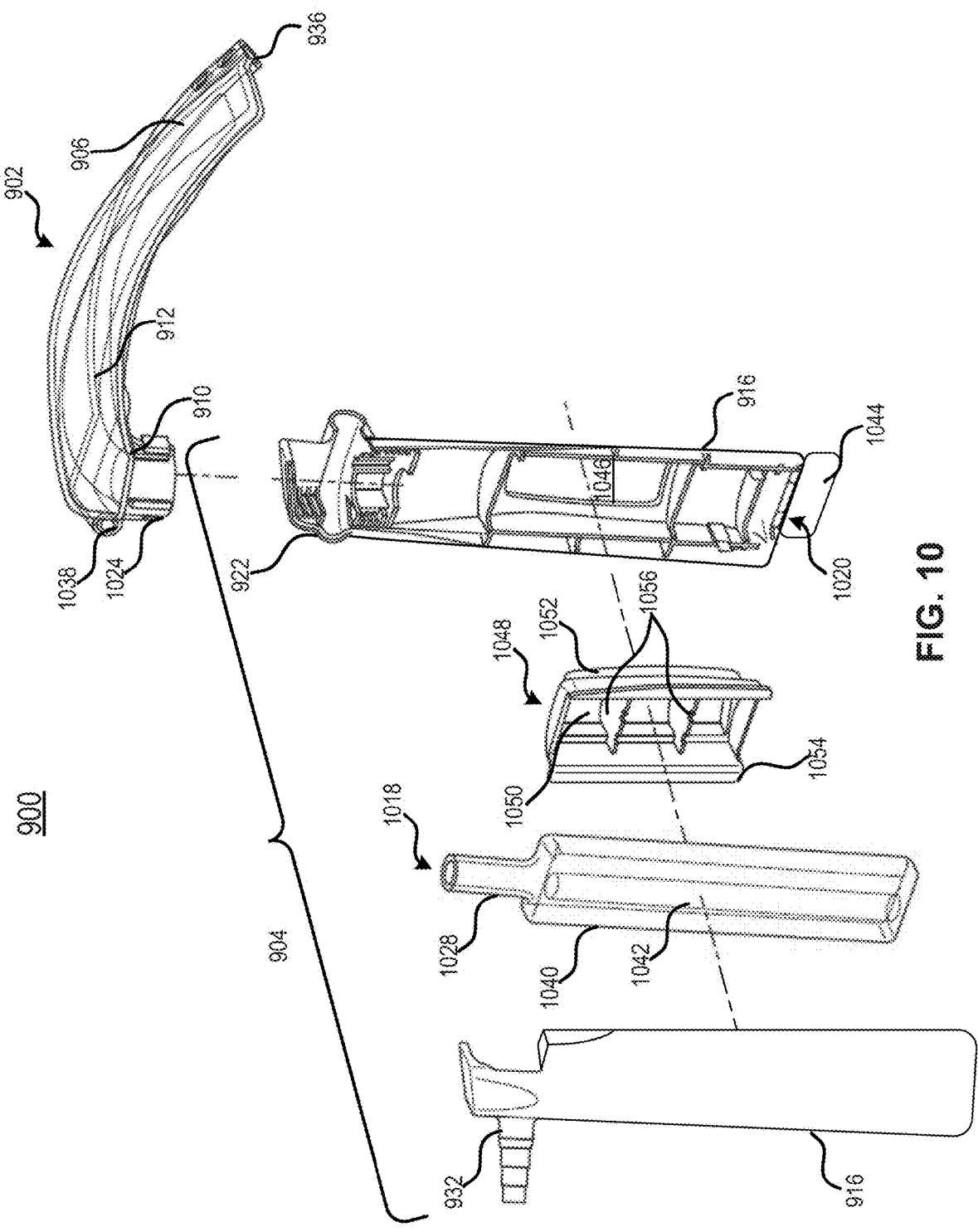
FIG. 10 is an exploded perspective view of the laryngoscope in FIG. 9 in accordance with an embodiment.

FIG. 10 is an exploded perspective view of laryngoscope 900 in FIG. 9 in accordance with an embodiment. In this embodiment, blade 902 includes a connector 1024 at proximal end 910, as well as an inlet 1038 of auxiliary channel 906. Connector 1024 of blade 902 can be snapped into connector 922 of handle 904 so that blade 902 is removably attached to handle 904. Inlet 1038 of auxiliary channel 906 is coupled to an end of adaptor 932 once blade 902 is attached to handle 904 so that a path is formed from adaptor 932 to outlet 936 of auxiliary channel 906.

Handle 904 includes a non-electric light source, e.g., chemiluminescent light source 1018 having a non-electric light source, e.g., chemiluminescent cartridge 1040 made from, for example, a flexible plastic material. A chemiluminescence reagent is stored in chemiluminescent cartridge 1040. Chemiluminescent cartridge 1040 also includes a vial 1042 of a catalyst agent. The chemiluminescence reagent and catalyst agent may be any suitable chemicals for chemiluminescent reactions depending on the desired wavelength of the light to be generated. In one example, the chemiluminescence reagent may be luminol and hydrogen peroxide and the catalyst agent may be iron, copper, or an auxiliary oxidant, which when mixed, can produce light in different colors in the visible light wavelengths. In another example, the light in the infrared wavelengths can be generated by any known infrared chemiluminescence reactions of chemiluminescence reagent and catalyst agent. It is to be appreciated that although one vial 1042 are shown in FIG. 10, any number of vials may be placed inside chemiluminescent cartridge 1040 depending on the desired wavelength and/or luminosity of the light. For example, different types of catalyst agents may be included in different vials, or different amounts of catalyst agent of the same type may be included in various numbers of vials. Chemiluminescent light source 1018 further includes an interface 1028 that can be mechanically coupled in connector 1024 of blade 902 and transmit the light generated from chemiluminescent cartridge 1040 to light channel 912.

In this embodiment, handle 904 includes an opening 1020 at the bottom surface of enclosure 916. Chemiluminescent light source 1018 can be replaced by removing the used one from opening 1020 and inserting a new one from opening 1020. Handle 904 also includes a door 1044 that can lock chemiluminescent light source 1018 in enclosure 916 when door 1044 is closed. Handle 904 also includes an opening 1046 on the side surface of enclosure 916 and a pressure activator 1048.

In an embodiment, pressure activator 1048 includes an inside surface 1050, an outside surface 1052, and a lip 1054. Inside surface 1050 include bumps 1056. When assembled, pressure activator 1048 is inserted partially through opening 1046 from inside handle 904. Lip 1054 of pressure activator 1048 sits inside handle 904 adjacent opening 1046. Bumps 1056 on the inside surface 1050 can transfer pressure applied to outside surface 1052 of pressure activator 1048 to chemiluminescent cartridge 1040. As described above, as chemiluminescent cartridge 1040 is made from a flexible plastic material, pressure applied on it by bumps 1056 of pressure activator 1048 can crack vial 1042 of catalyst agent in chemiluminescent cartridge 1040. The catalyst agent released from vial 1042 then reacts with the chemiluminescence reagent in chemiluminescent cartridge 1040, which in turn generates light in any desired wavelength(s). As described below, mechanisms other than pressure activator 1048 may be applied as well to activate the chemiluminescence reactions.

Figure 11:
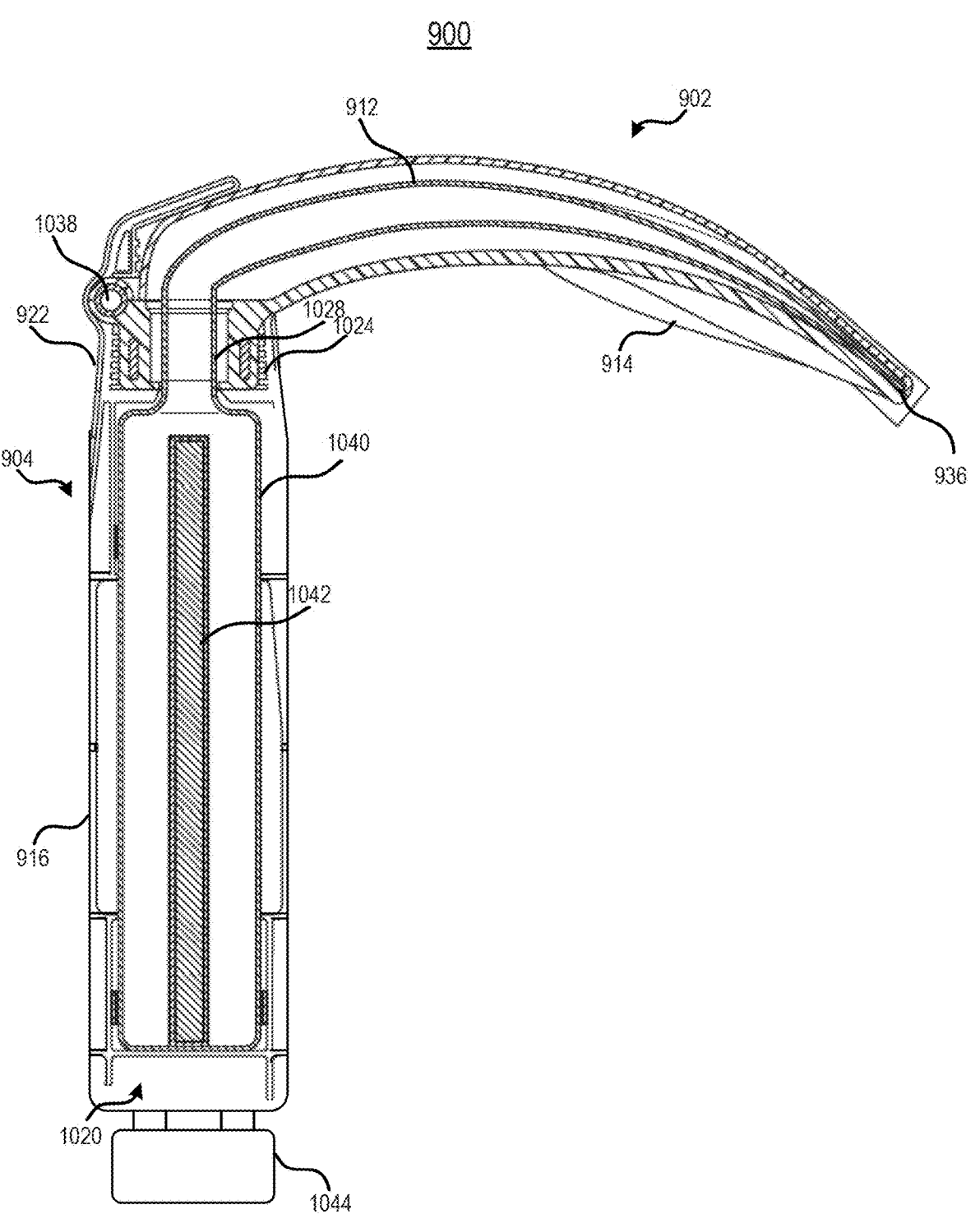
FIG. 11 is a side cross-sectional view of the laryngoscope in FIG. 9 along the line A-A in accordance with an embodiment.

FIG. 11 is a side cross-sectional view of laryngoscope 900 in FIG. 9 along the line A-A in accordance with an embodiment. As shown in FIG. 11, once being inserted from opening 1020, chemiluminescent light source 1018 resides in enclosure 916 of handle 904. Once connector 1024 of blade 902 is snapped into connector 922 of handle 904, interface 1028 of chemiluminescent light source 1018 is coupled to one end of light channel 912 of blade 902 to form an optical path for transmitting the light from chemiluminescent light source 1018.

Figure 12:
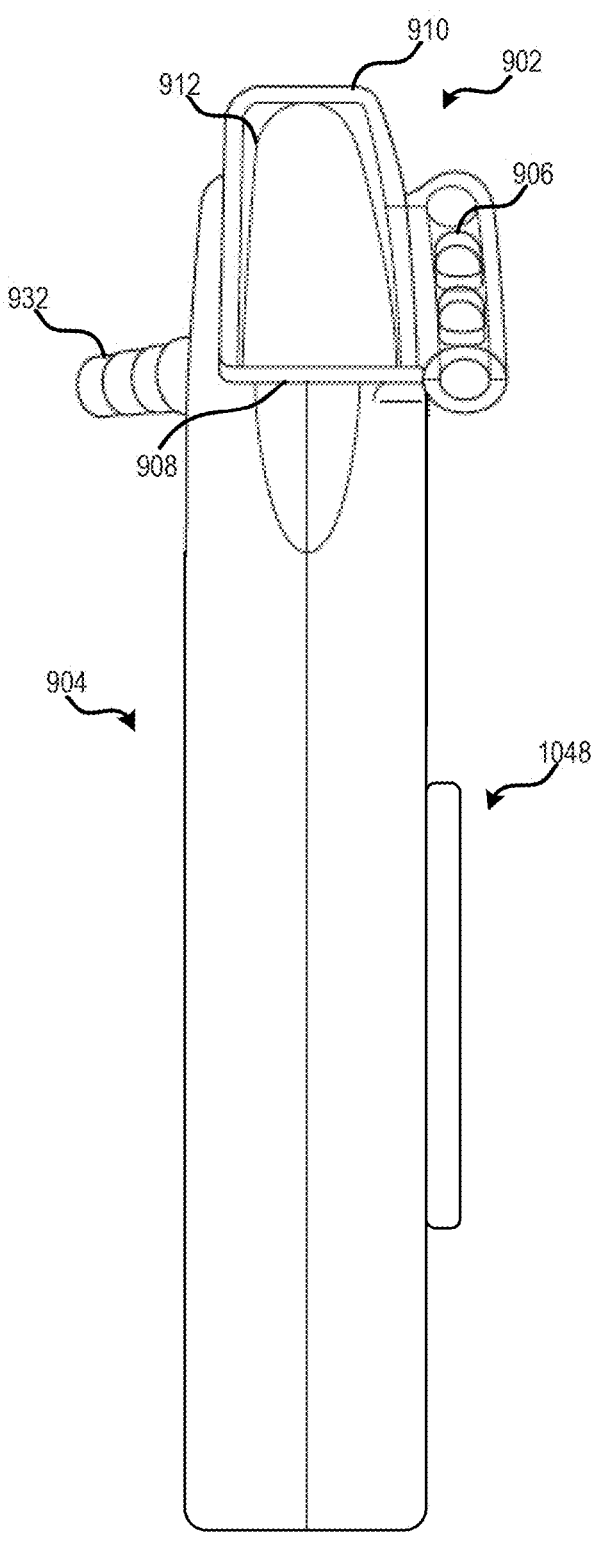
FIG. 12 is a front view of the laryngoscope in FIG. 9 in accordance with an embodiment.
Figure 13:
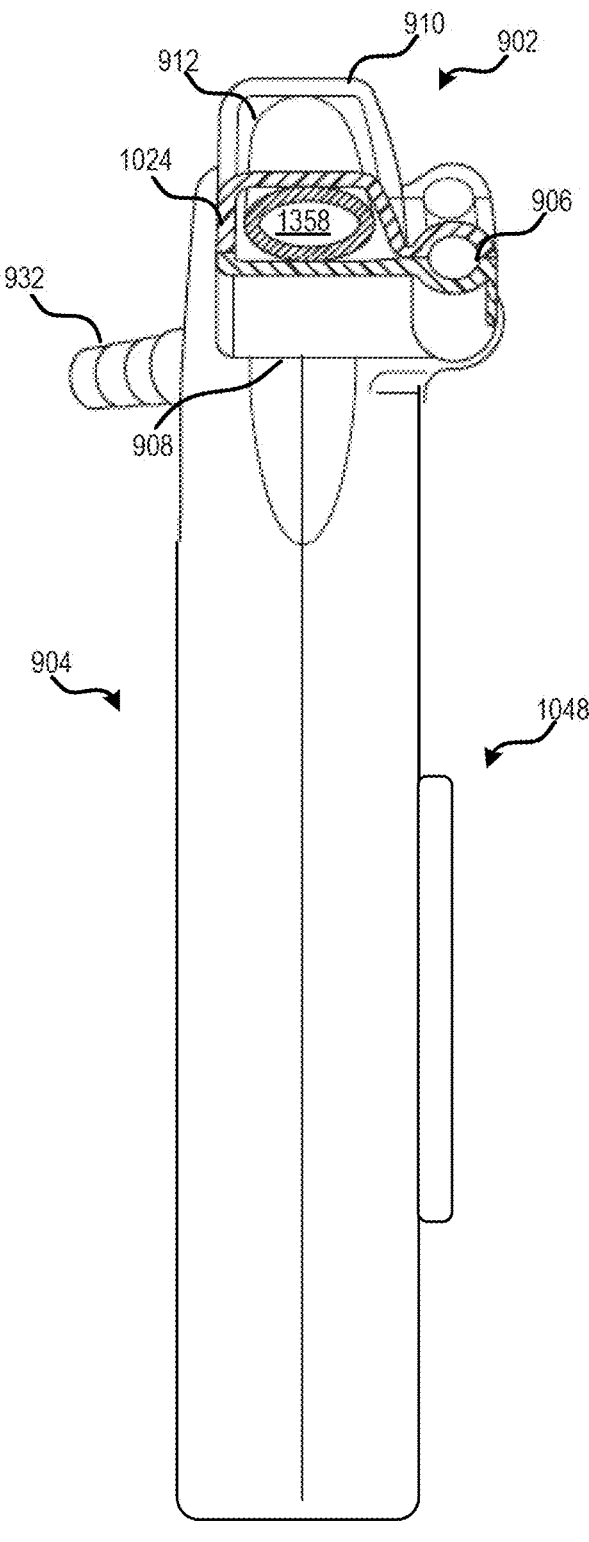
FIG. 13 is a front cross-sectional view of the laryngoscope in FIG. 9 along the line B-B in accordance with an embodiment.

FIG. 12 is a front view of laryngoscope 900 in FIG. 9 in accordance with an embodiment. FIG. 13 is a front cross-sectional view of laryngoscope 900 in FIG. 9 along the line B-B in accordance with an embodiment. In this embodiment, light channel 912 is disposed in the middle of blade 902 in the width direction, and auxiliary channel 906 is disposed at the edge of blade 902. An optical fiber or a waveguide 1358 is inserted into light channel 912 as the medium for light transmission. Auxiliary channel 906 is used as an oxygen channel or a negative pressure channel for suction. In some embodiments, an instrumentation, such as a wire, may be inserted into auxiliary channel 906.

Figure 14:
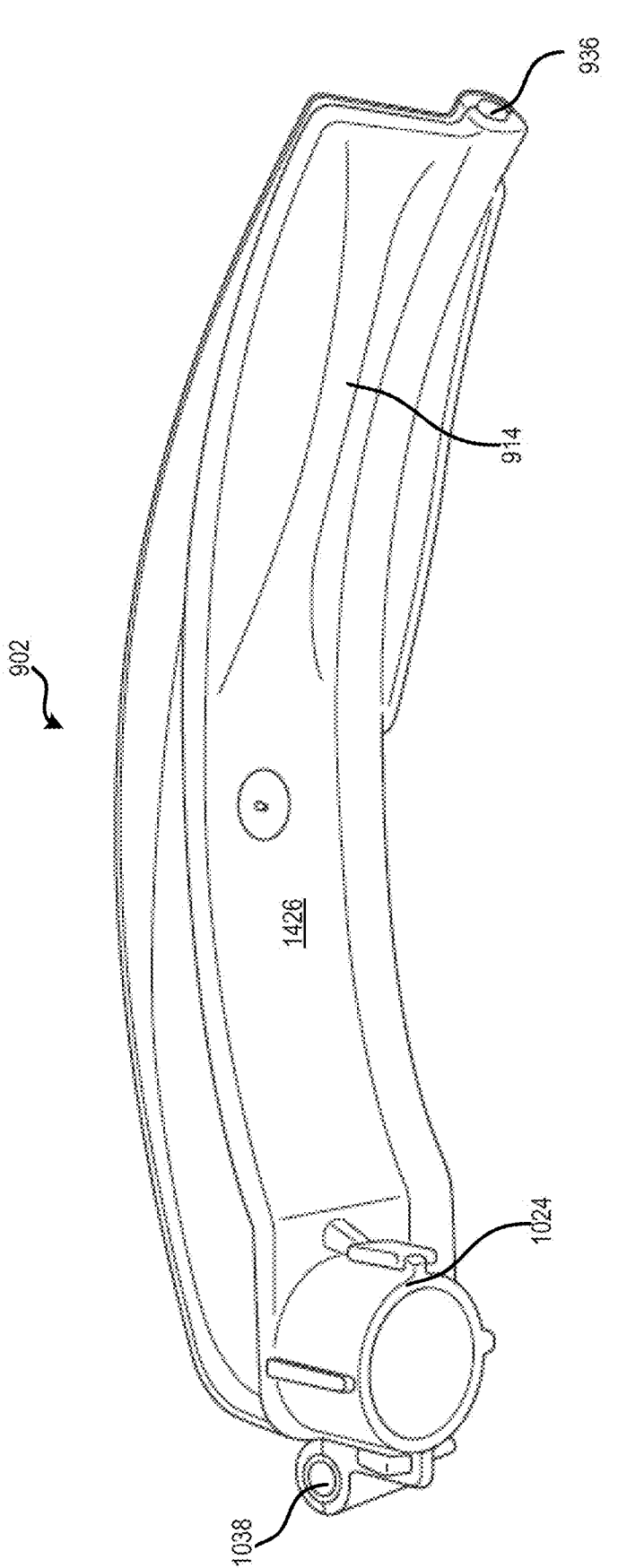
FIG. 14 is a perspective view of a blade of the laryngoscope in FIG. 9 in accordance with an embodiment.
Figure 15:
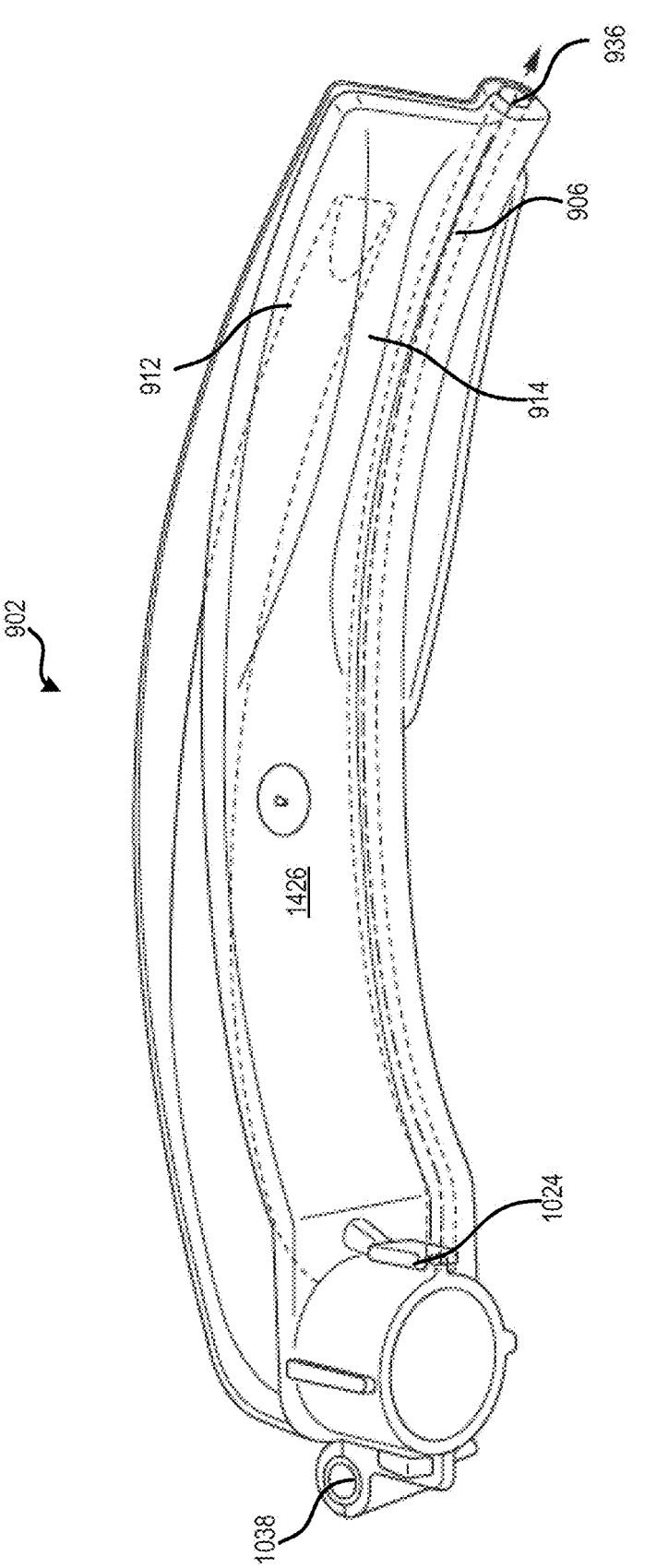
FIG. 15 is another perspective view of a blade of the laryngoscope in FIG. 9 in accordance with an embodiment.

FIGS. 14 and 15 are perspective views of blade 902 of laryngoscope 900 in FIG. 9 in accordance with an embodiment. In this embodiment, a reflective surface 1426 at the bottom of blade 902 is formed by high-reflection coatings to enhance luminosity. Auxiliary channel 906 in blade 902 extends from inlet 1038 to outlet 936 along the length of blade 902. Auxiliary channel 906 is proximate to light channel 912 in blade 902.

Figure 16:
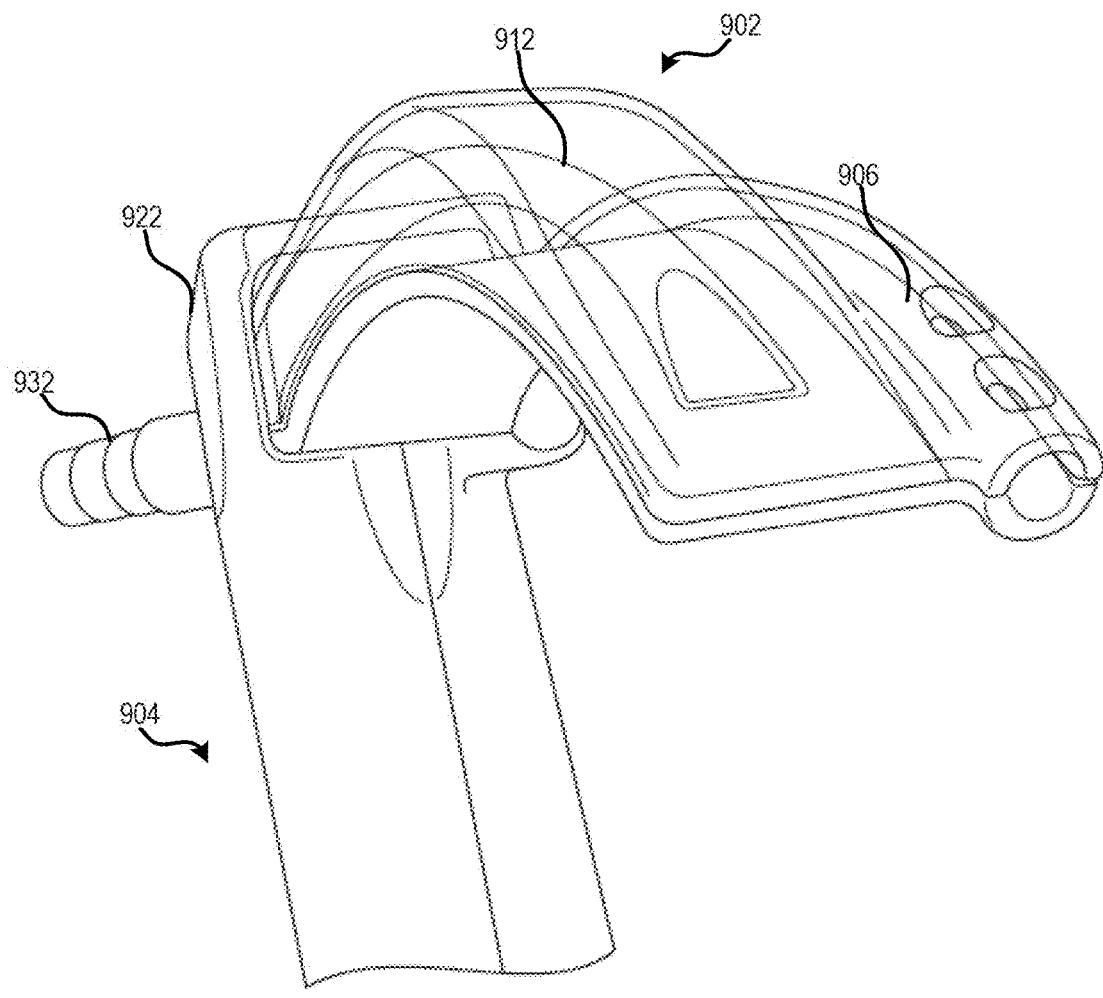
FIG. 16 is a perspective view of a blade and a connector of the laryngoscope in FIG. 9 in accordance with an embodiment.
Figure 17:
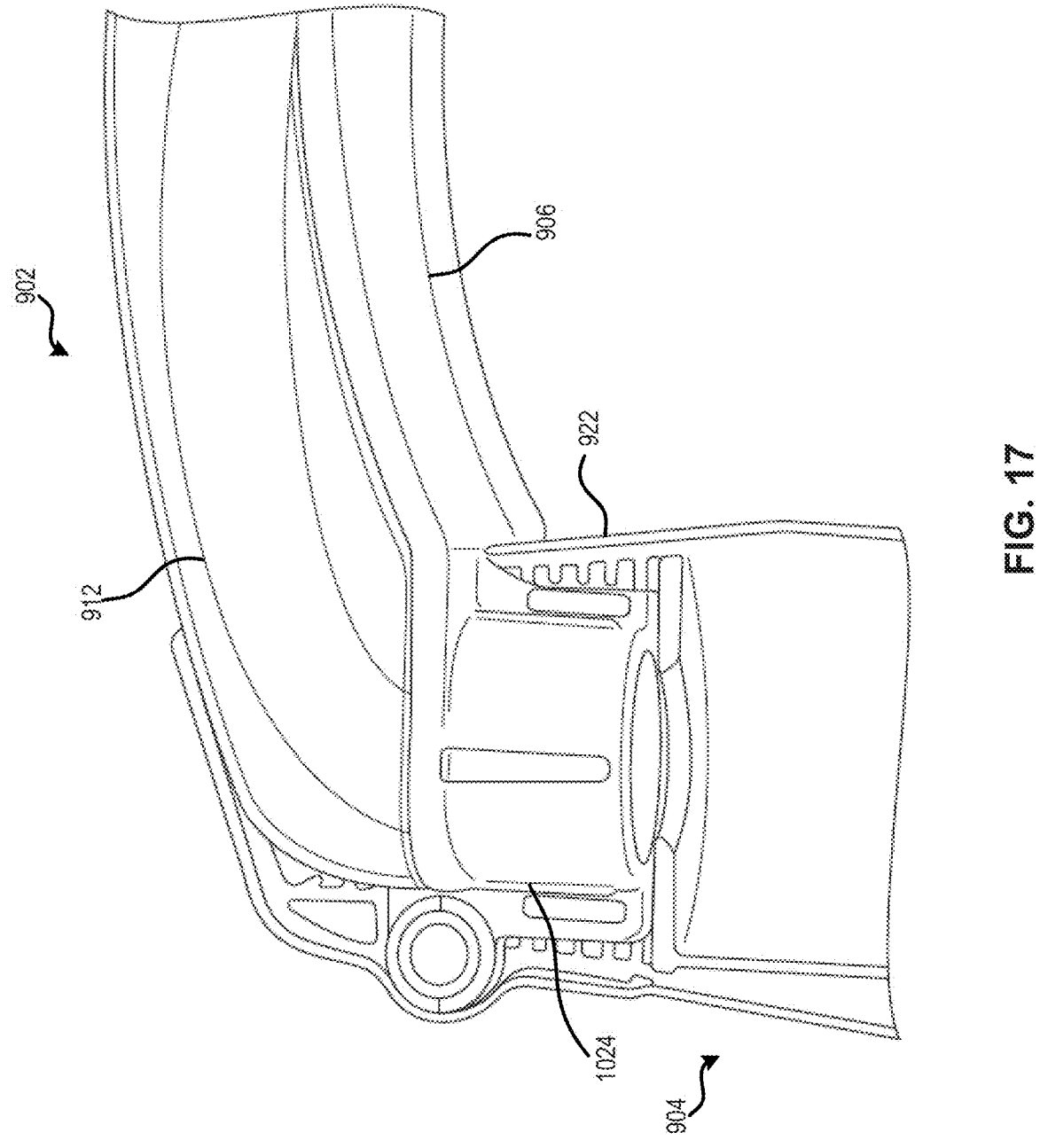
FIG. 17 is a side cross-sectional view of a blade and a connector of the laryngoscope in FIG. 9 in accordance with an embodiment.

FIGS. 16 and 17 are perspective view and side cross-sectional view, respectively, of blade 902 and connectors 922 and 1024 of laryngoscope 900 in FIGS. 9 and 10 in accordance with an embodiment. In this embodiment, connectors 922 and 1024 are configured to removably attach blade 902 to handle 904. As a result, light channel 912 in blade 902 can be coupled to chemiluminescent light source 1018 (shown in FIG. 10) in handle 904, and auxiliary channel 906 in blade 902 can be coupled to adaptor 932 on handle 904.

Figure 18:
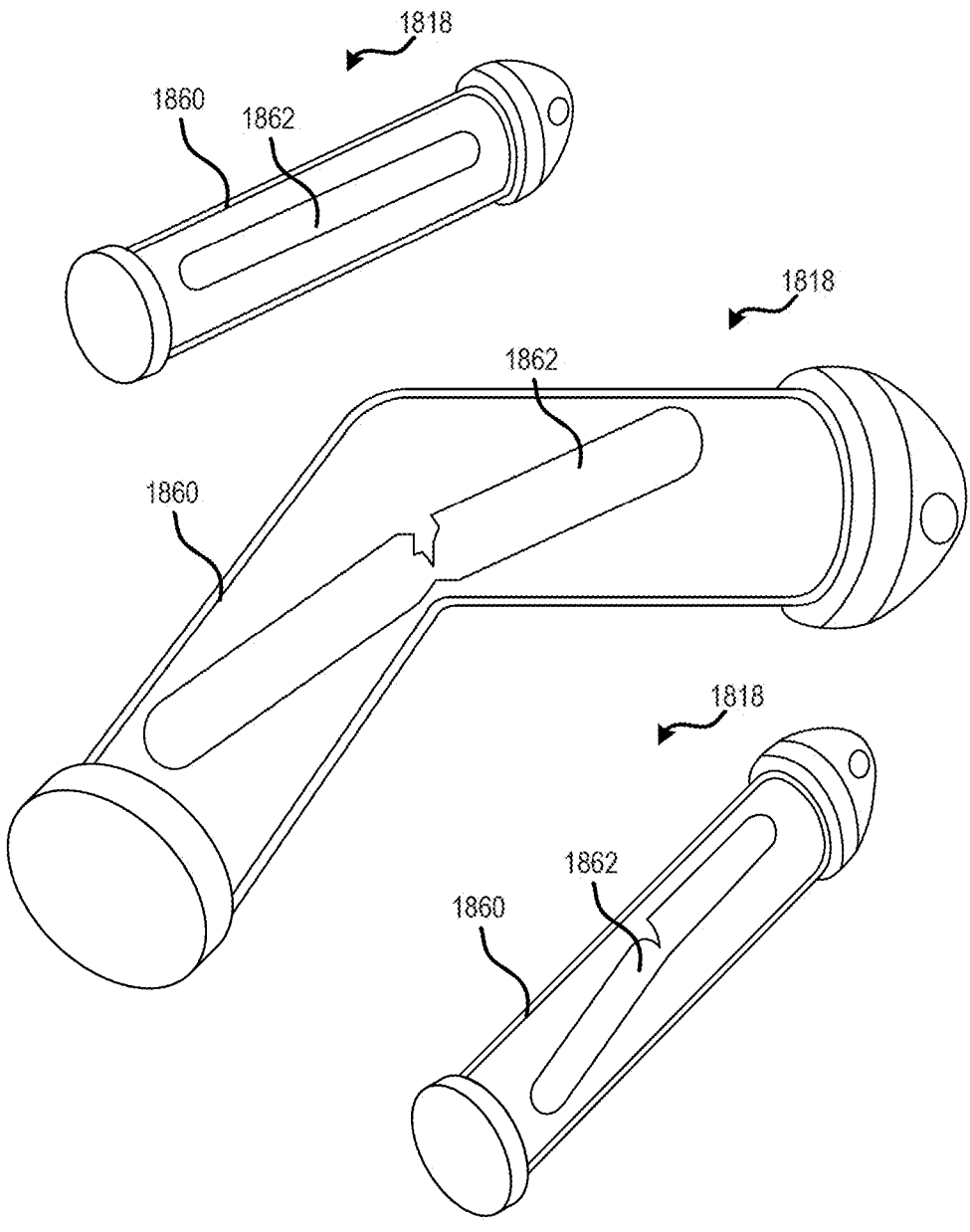
FIG. 18 is a depiction of an example of activation of a chemiluminescent light source in a handle of a laryngoscope in accordance with an embodiment.

FIG. 18 is a depiction of an example of activation of a non-electric, e.g., chemiluminescent, light source 1818 in a handle of a laryngoscope in accordance with an embodiment. Chemiluminescent light source 1818 in this embodiment is one example of non-electric light source 118 in FIG. 1. In this embodiment, chemiluminescent light source 1818 includes a chemiluminescent cartridge 1860 containing a chemiluminescence reagent and a vial 1862 of a catalyst agent. Chemiluminescent light source 1818 is activated prior to being inserted into the handle of a laryngoscope, for example, by bending chemiluminescent cartridge 1860 to break vial 1862. The catalyst agent released from the broken vial 1862 reacts with the chemiluminescence reagent in chemiluminescent cartridge 1860 to generate light in any desired wavelength(s) as described above. Once activated, chemiluminescent light source 1818 may be inserted into the handle of a laryngoscope.

Figure 19:
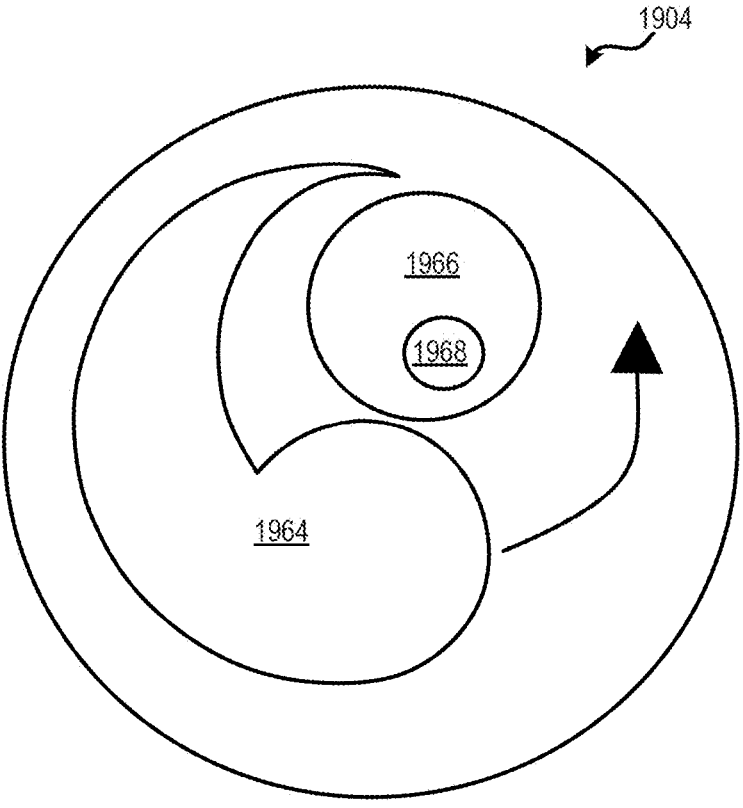
FIG. 19 is a schematic illustration of an example of rotational activation of a chemiluminescent light source in a handle of a laryngoscope by a cam in accordance with an embodiment.
Figure 20:
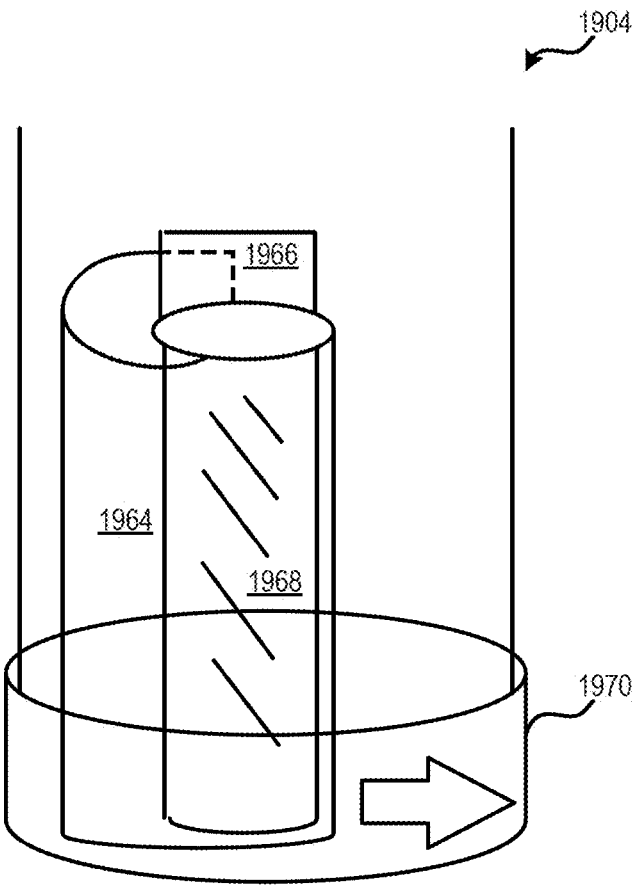
FIG. 20 is a depiction of an example of a cam for rotational activation of a chemiluminescent light source of a laryngoscope in accordance with an embodiment.

FIGS. 19 and 20 are schematic illustrations of an example of rotational activation of a chemiluminescent light source in a handle 1904 of a laryngoscope by a cam 1964 in accordance with an embodiment. Handle 1904 in this embodiment is one example of handle 104 in FIG. 1. In this embodiment, after receiving the chemiluminescent light source, a base 1970 of handle 1904 of a laryngoscope can rotate with respect to a chemiluminescent cartridge 1966 inside handle 1904. The rotation of base 1970 can cause the rotation of cam 1964 against chemiluminescent cartridge 1966 as well, which will make sliding contact with chemiluminescent cartridge 1966 until cracking a vial 1968 of catalyst agent in chemiluminescent cartridge 1966. That is, torsional pressure may be applied by rotating base 1970 of handle 1904 via cam 1964 to crack vial 1968 of catalyst agent in chemiluminescent cartridge 1966. As a result, the catalyst agent released from cracked vial 1968 reacts with the chemiluminescence reagent in chemiluminescent cartridge 1966 to generate light in any desired wavelength(s) as described above. In this embodiment, cam 1964 is in a "comma" shape in the plan view as shown in FIG. 19. The "comma" shape of cam 1964 may increase the torsional pressure applied by cam 1964 to more easily crack vial 1968. It is understood that, however, the shape of cam 1964 is not limited to the "comma" shape, but can be any suitable shape, such as, but not limited to, round, semi-circular, oval, etc. It is to be appreciated that in some embodiments, a rotating mechanism other than base 1970 of handle 1904 may be used to apply the torsional pressure. Thus, the chemiluminescent light source may be activated prior to being inserted into handle 1904 of the laryngoscope.

Figure 21:
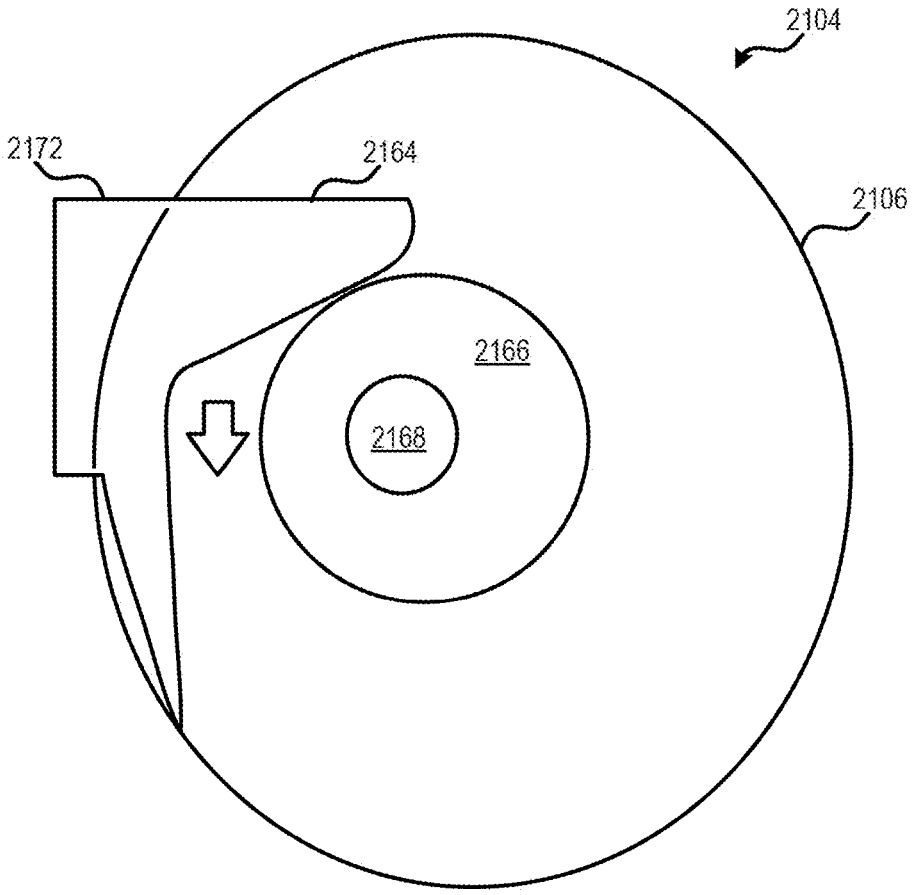
FIG. 21 is a schematic illustration of an example of horizontal activation of a chemiluminescent light source in a handle of a laryngoscope by a cam in accordance with an embodiment.
Figure 22:
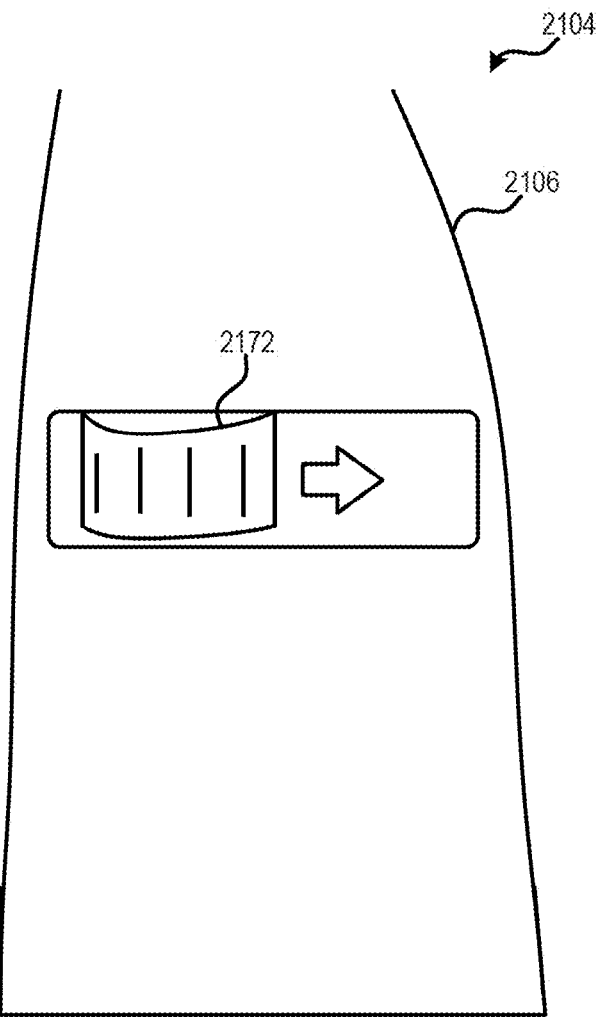
FIG. 22 is a depiction of an example of a horizontal trigger for horizontal activation of a chemiluminescent light source of a laryngoscope in accordance with an embodiment.

FIGS. 21 and 22 are schematic illustrations of an example of horizontal activation of a chemiluminescent light source in handle 2104 of a laryngoscope by a cam 2164 in conjunction with a horizontal trigger 2172, in accordance with an embodiment. Handle 2104 in this embodiment is one example of handle 104 in FIG. 1. In this embodiment, after receiving the chemiluminescent light source, horizontal trigger 2172 on an enclosure 2106 of handle 2104 of the laryngoscope can slide, i.e., horizontally move with respect to a chemiluminescent cartridge 2166 inside handle 2104. The movement of horizontal trigger 2172 can cause the movement of cam 2164 against chemiluminescent cartridge 2166, which will make sliding contact with chemiluminescent cartridge 2166 until cracking a vial 2168 of catalyst agent in chemiluminescent cartridge 2166. That is, pressure may be applied by sliding horizontal trigger 2172 via cam 2164 to crack vial 2168 of catalyst agent in chemiluminescent cartridge 2166. As a result, the catalyst agent released from cracked vial 2168 reacts with the chemiluminescence reagent in chemiluminescent cartridge 2166 to generate light in any desired wavelength(s) as described above. It is understood that the shape of cam 2164 is not limited to the shape shown in FIG. 21, but can be any suitable shape, such as, but not limited to, round, semi-circular, oval, etc.

Figure 23:
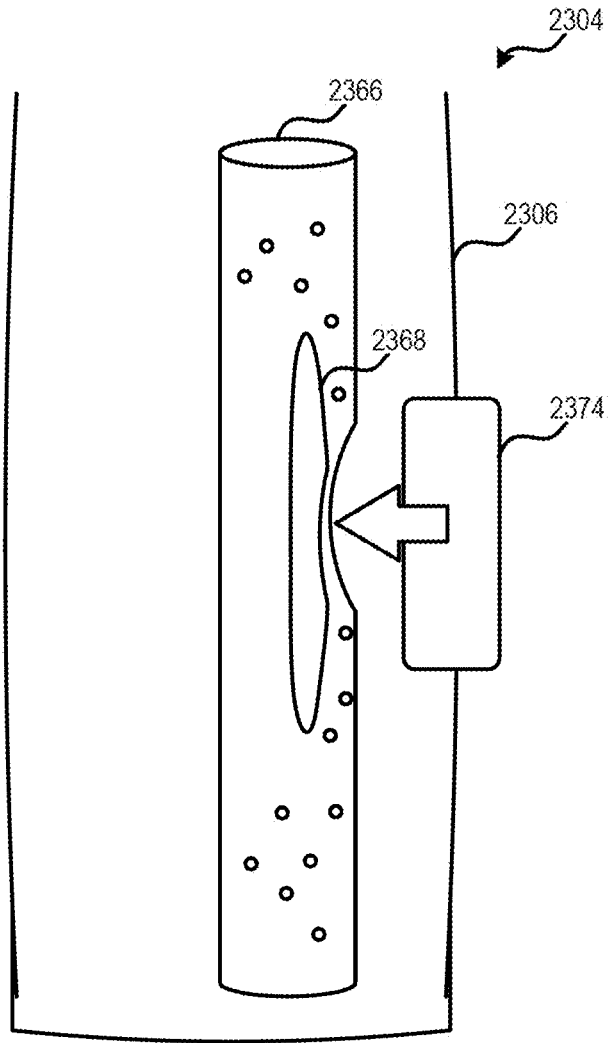
FIG. 23 is a schematic illustration of an example of pressure activation of a chemiluminescent light source in a handle of a laryngoscope in accordance with an embodiment.

FIG. 23 is a schematic illustration of an example of pressure activation of a chemiluminescent light source in a handle 2304 of a laryngoscope by a pressure activator 2374 in accordance with an embodiment. Handle 2304 in this embodiment is one example of handle 104 in FIG. 1. In this embodiment, after receiving the chemiluminescent light source including a chemiluminescent cartridge 2366, pressure activator 2374 on an enclosure 2306 of handle 2304 of the laryngoscope can be pressed toward chemiluminescent cartridge 2366. The movement of pressure activator 2374 can crack a vial 2368 of catalyst agent in chemiluminescent cartridge 2366. As a result, the catalyst agent released from cracked vial 2368 reacts with the chemiluminescence reagent in chemiluminescent cartridge 2366 to generate light in any desired wavelength(s) as described above. Pressure activator 2374 in this example is similar to pressure activator 1048 described above in the embodiment in FIGS. 9-17.

Figure 24:
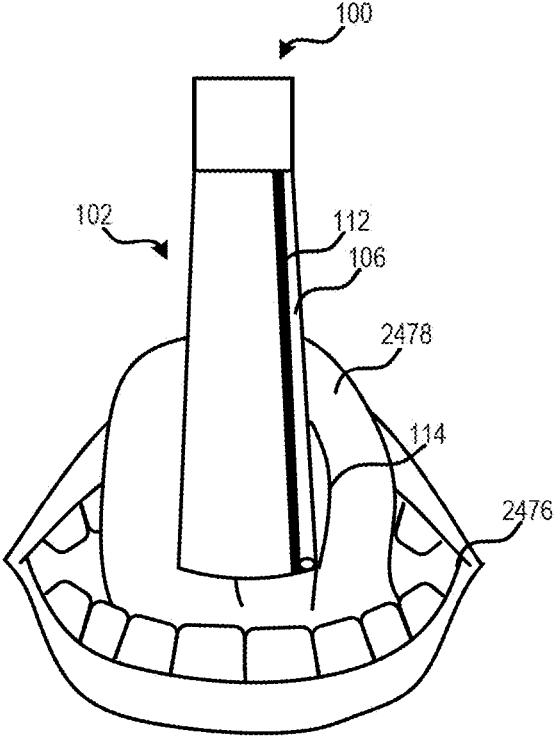
FIG. 24 is a depiction of an example of intubation of a laryngoscope in the mouth in accordance with an embodiment.

FIG. 24 is a depiction of an example of intubation of laryngoscope 100 in a mouth 2476 in accordance with an embodiment. In operation, the operator may hold handle 104 (as shown in FIG. 1) and insert at least a part of blade 102 into the patient's mouth 2476 at a desired position. The operator can also use lateral ridge 114 of blade 102 to capture tongue 2478 of the patient and move tongue 2478 to optimize the field of vision. To get better visualization of mouth 2476 and the larynx, the operator can activate the non-electric light source to generate light at a wavelength transmitting along light channel 112, which illuminates mouth 2476 and the larynx of the patient. Blade 102 may be transparent with the exception of the bottom, which is reflective to enhance luminosity. The reaction time of non-electric light source 118 can last for hours, providing sufficient time to intubate the patient in either an elective or emergent situation. The materials used in non-electric light source 118 are Food and Drug Administration (FDA) approved as being non-toxic, should any materials be inhaled or ingested by the patient.

Figure 25:
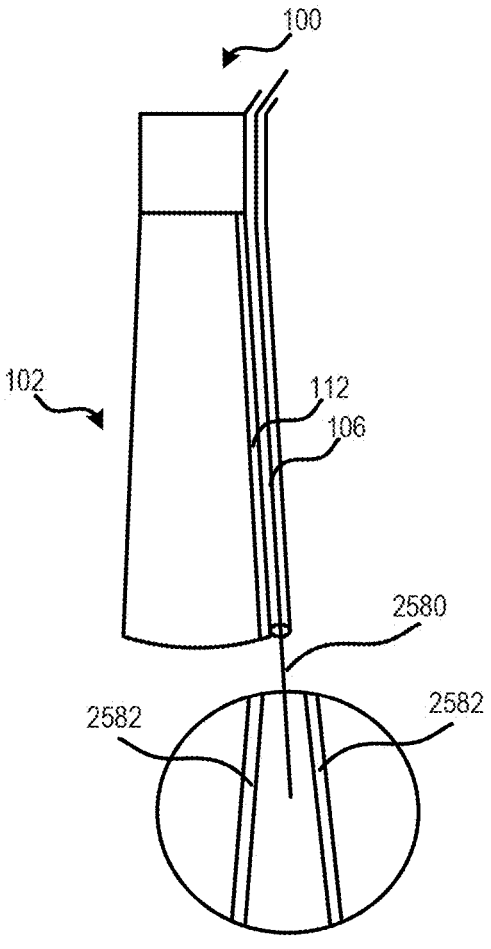
FIG. 25 is a depiction of an example of insertion of a wire via a channel of a laryngoscope in accordance with an embodiment.

FIG. 25 is a depiction of an example of insertion of a wire 2580 via auxiliary channel 106 of laryngoscope 100 in accordance with an embodiment. In this embodiment, the operator may insert wire 2580 past vocal cords 2582 of the patient via auxiliary channel 106 during the procedures. As described above, depending on the needs, the operator can replace wire 2580 with any suitable instrumentations, such as a cautery device, a laser, a fiber optics, a biopsy forceps, placement of radiotherapeutic markers and materials, a wire guided scalpel, placement of topical medications and therapies, etc. Should there be any difficulty in identifying vocal cords 2582, the operator may continue to provide a stream of life-saving oxygen via auxiliary channel 106 during the procedures. Additionally or alternatively, if the mouth or the larynx of the patient is contaminated with blood, mucus, etc., suction may be applied via auxiliary channel 106. This can be achieved without removing laryngoscope 100 and keeps the operator's hand(s) free.

It is to be appreciated that the Detailed Description section, and not the Summary and Abstract sections, is intended to be used to interpret the claims. The Summary and Abstract sections may set forth one or more but not all exemplary embodiments of this disclosure as contemplated by the inventor(s), and thus, are not intended to limit this disclosure or the appended claims in any way.

While this disclosure has been described herein with reference to exemplary embodiments for exemplary fields and applications, it should be understood that this disclosure is not limited thereto. Other embodiments and modifications thereto are possible, and are within the scope and spirit of the present disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. In addition, alternative embodiments may perform functional blocks, steps, operations, methods, etc. using orderings different from those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of this disclosure should not be limited by any of the above-described exemplary embodiments, but should be defined only in accordance with the following claims and their equivalents.

What is claimed is:

1. A laryngoscope, comprising:
a curved blade comprising:
  a proximal end,
  a distal end comprising a first channel terminal part and a second channel terminal part, the second channel terminal part being separate from the first channel terminal part,
  a first channel, and
  a second channel disposed proximate and through the blade and configured to provide at least one of oxygen, suction, and an instrumentation into the proximal end and out of the distal end of the blade; and a handle coupled to the proximal end of the blade, the handle comprising:
  an enclosure comprising a first opening on a side surface of the enclosure and a second opening on a bottom surface of the enclosure;
  a removable non-electric light source configured to be inserted into the enclosure through the second opening, the removable non-electric light source comprising a chemiluminescent light source; and
  a pressure activator partially inserted through the first opening, the pressure activator comprising a plurality of bumps on an inside surface of the pressure activator facing the removable non-electric light source, wherein the plurality of bumps are configured to, in response to the pressure activator being pressed, crack a vial of a catalytic agent in the chemiluminescent light source to generate light that transmits along the first channel.

2. The laryngoscope of claim 1, wherein at least a part of the blade is reflective to the light.

3. The laryngoscope of claim 1, wherein the blade widens out from the proximal end to the distal end.

4. The laryngoscope of claim 1, wherein the blade comprises a lateral ridge configured to facilitate capture and direction of a tongue.

5. The laryngoscope of claim 1, wherein the first channel includes an optical fiber or a waveguide.

6. The laryngoscope of claim 1, wherein the handle further comprises at least one connector configured to removably attach the blade to the handle.

7. The laryngoscope of claim 6, wherein the at least one connector comprises an optical interface configured to couple the light generated by the chemiluminescent light source to the first channel.

8. The laryngoscope of claim 6, wherein the at least one connector comprises an adaptor configured to couple an oxygen source, a suction source, or the instrumentation to the second channel.

9. The laryngoscope of claim 1, wherein the second channel traverses a length of the blade.

10. The laryngoscope of claim 1, wherein the second channel is proximate to the first channel.

11. The laryngoscope of claim 1, wherein the instrumentation comprises one or more of a wire, a cautery device, a laser, a fiber optics, a biopsy forceps, placement of radiotherapeutic markers and materials, a wire guided scalpel, or placement of topical medications and therapies.

12. A handle of a laryngoscope, comprising:
an enclosure comprising a first opening on a side surface of the enclosure and a second opening on a bottom surface of the enclosure;
a removable non-electric light source configured to be inserted into the enclosure through the second opening, the removable non-electric light source comprising a chemiluminescent light source; and
a pressure activator partially inserted through the first opening from inside the enclosure, the pressure activator comprising a plurality of bumps on an inside surface of the pressure activator facing the removable non-electric light source,
wherein a catalytic agent in the chemiluminescent light source is configured to be activated by pressure from the plurality of bumps in response to the pressure activator being pressed to generate light.

13. The handle of claim 12, further comprising a connector configured to removably attach a blade to the handle, the connector comprising an optical interface configured to couple the light generated by the chemiluminescent light source to a light channel on the blade.

14. The handle of claim 12, further comprising a connector configured to removably attach a blade to the handle, the connector comprising an adaptor configured to couple an oxygen source, a suction source, or instrumentation to an auxiliary channel on the blade.

\* \* \* \* \*